United States Patent
Zarembo

(10) Patent No.: US 7,930,038 B2
(45) Date of Patent: Apr. 19, 2011

(54) TUBULAR LEAD ELECTRODES AND METHODS

(75) Inventor: Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 488 days.

(21) Appl. No.: 11/140,101

(22) Filed: May 27, 2005

(65) Prior Publication Data

US 2007/0038278 A1    Feb. 15, 2007

(51) Int. Cl.
*A61N 1/00* (2006.01)
(52) U.S. Cl. .................................... 607/116
(58) Field of Classification Search .......... 607/116–118, 607/122; 600/370–374
See application file for complete search history.

(56) References Cited

U.S. PATENT DOCUMENTS

| | | | | |
|---|---|---|---|---|
| 4,033,355 A * | 7/1977 | Amundson | ................... | 607/122 |
| 4,559,951 A * | 12/1985 | Dahl et al. | ................... | 600/374 |
| 5,279,299 A * | 1/1994 | Imran | ............................ | 600/393 |
| 5,755,764 A * | 5/1998 | Schroeppel | ................... | 607/122 |
| 6,205,361 B1 * | 3/2001 | Kuzma et al. | ................. | 607/116 |
| 6,285,910 B1 * | 9/2001 | Verness et al. | ................. | 607/122 |
| 6,322,559 B1 * | 11/2001 | Daulton et al. | ................. | 606/41 |
| 6,493,590 B1 * | 12/2002 | Wessman et al. | ............. | 607/116 |
| 6,505,401 B1 * | 1/2003 | Doan | .............................. | 29/860 |
| 6,522,932 B1 * | 2/2003 | Kuzma et al. | ................. | 607/116 |
| 6,785,576 B2 * | 8/2004 | Verness | ........................ | 607/122 |
| 6,836,687 B2 | 12/2004 | Kelley et al. | | |
| 6,915,169 B2 * | 7/2005 | Flynn et al. | ................... | 607/122 |
| 7,177,702 B2 * | 2/2007 | Wallace et al. | ............... | 607/117 |
| 2004/0176810 A1 | 9/2004 | Stadler et al. | | |

* cited by examiner

*Primary Examiner* — Niketa I Patel
*Assistant Examiner* — Nicole F Lavert
(74) *Attorney, Agent, or Firm* — Faegre & Benson LLP

(57) ABSTRACT

This document discusses, among other things, a lead assembly including an implantable lead body including a lumen, a conductor extending through the lumen in the lead body, and an electrode including a tube having an internal surface. In an example, at least a portion of the tube is formed into a helix. The conductor is electrically coupled to the internal surface of the first tube. An example method includes winding a tubular electrode around a mandrel, extending a conductor through a lumen in a lead body for a medical device lead assembly, and extending the conductor into the tubular electrode.

27 Claims, 24 Drawing Sheets

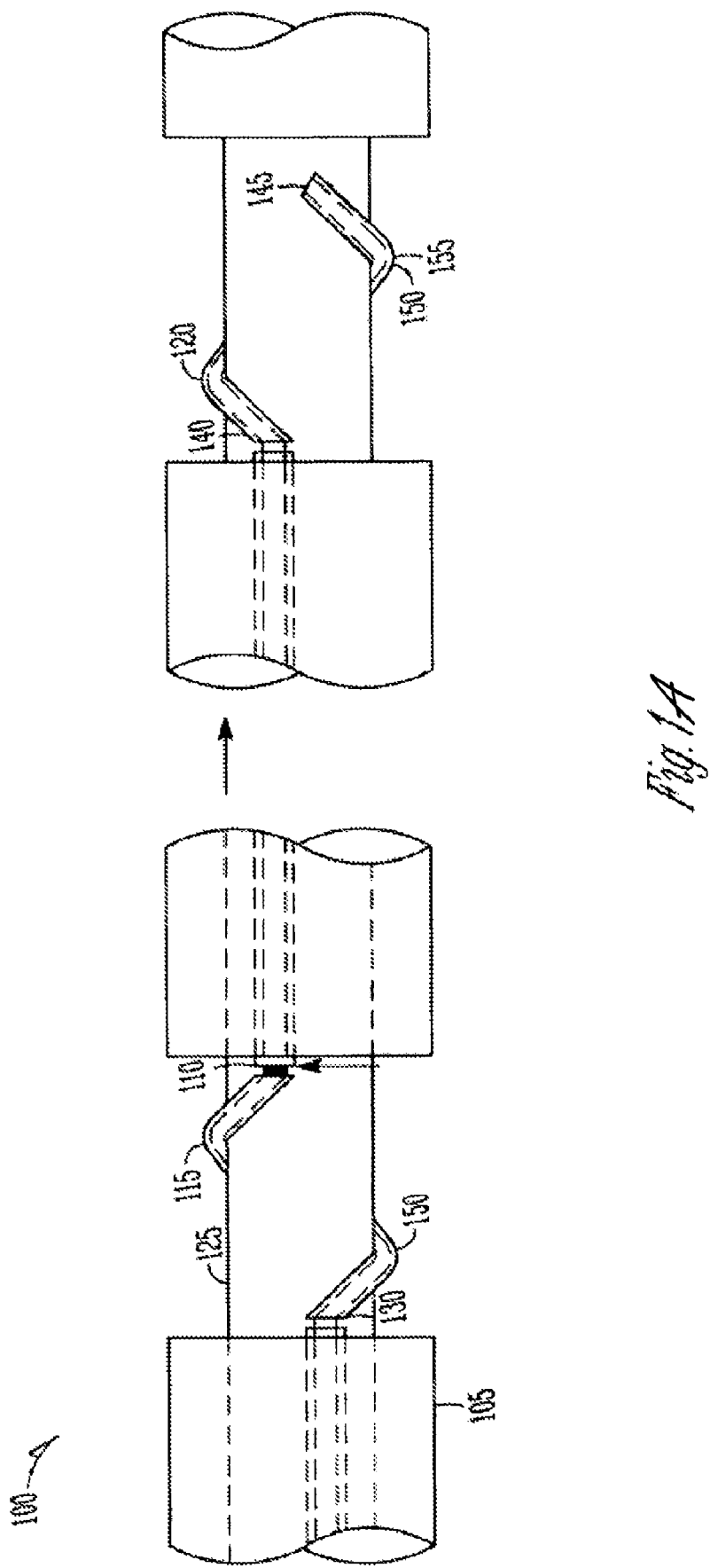

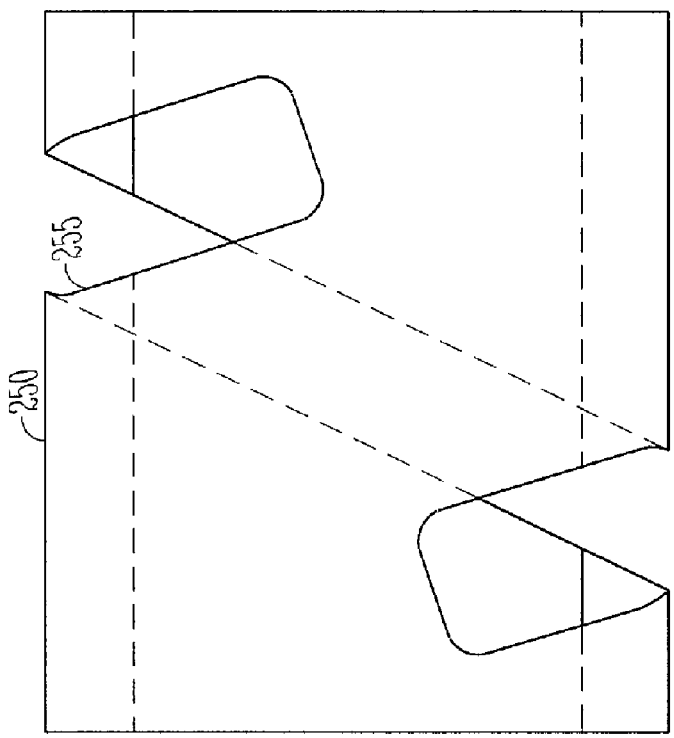
Fig. 2H
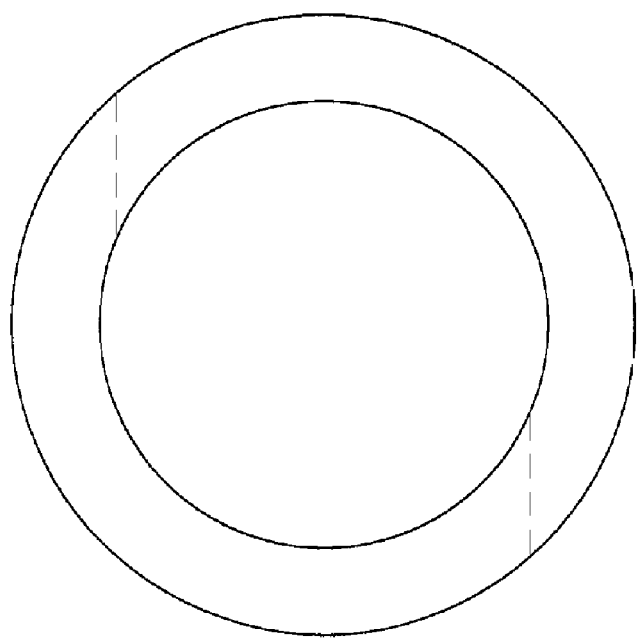

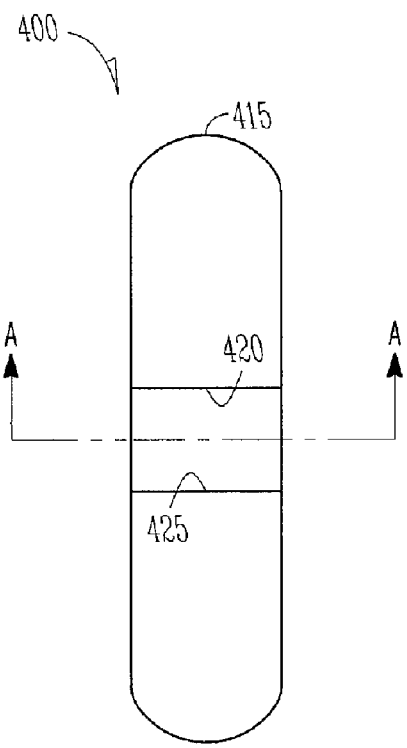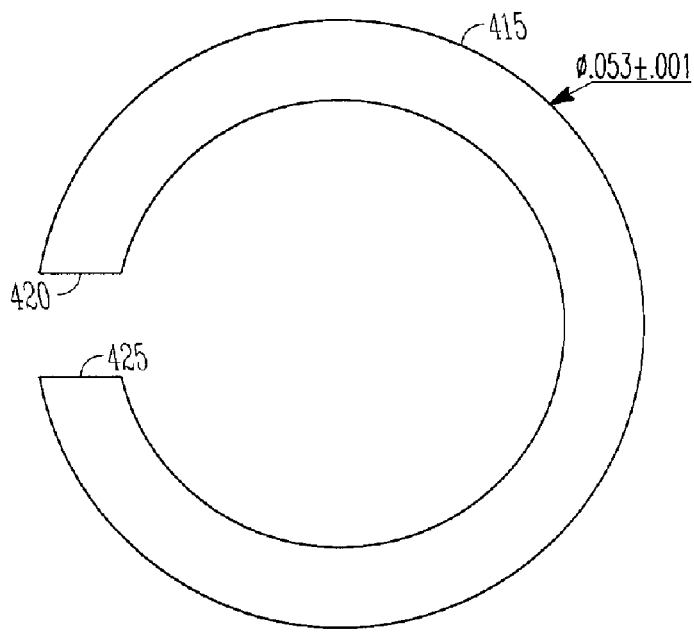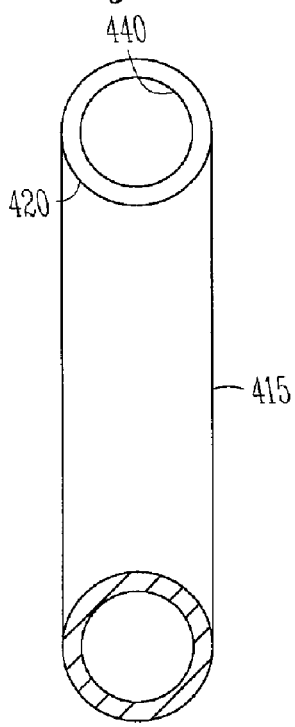
Fig. 4A
Fig. 4C
Fig. 4B

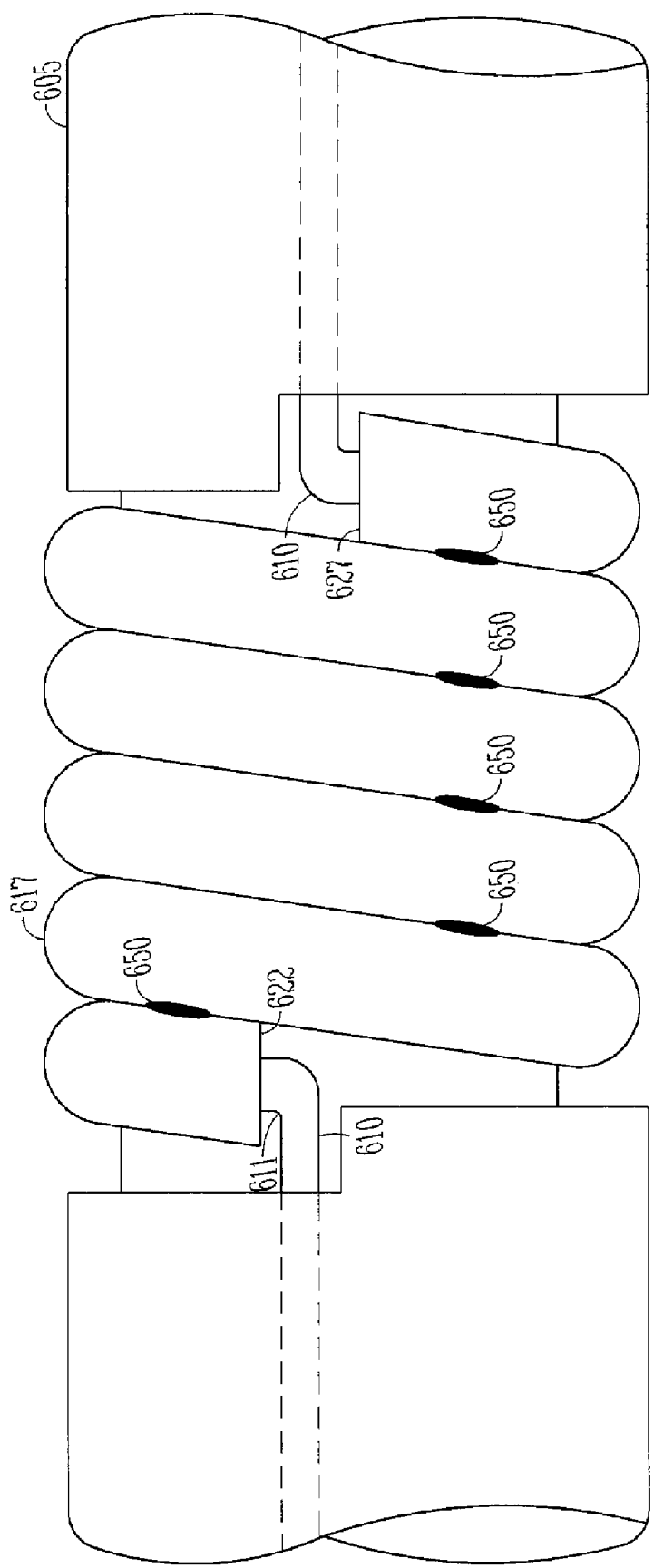

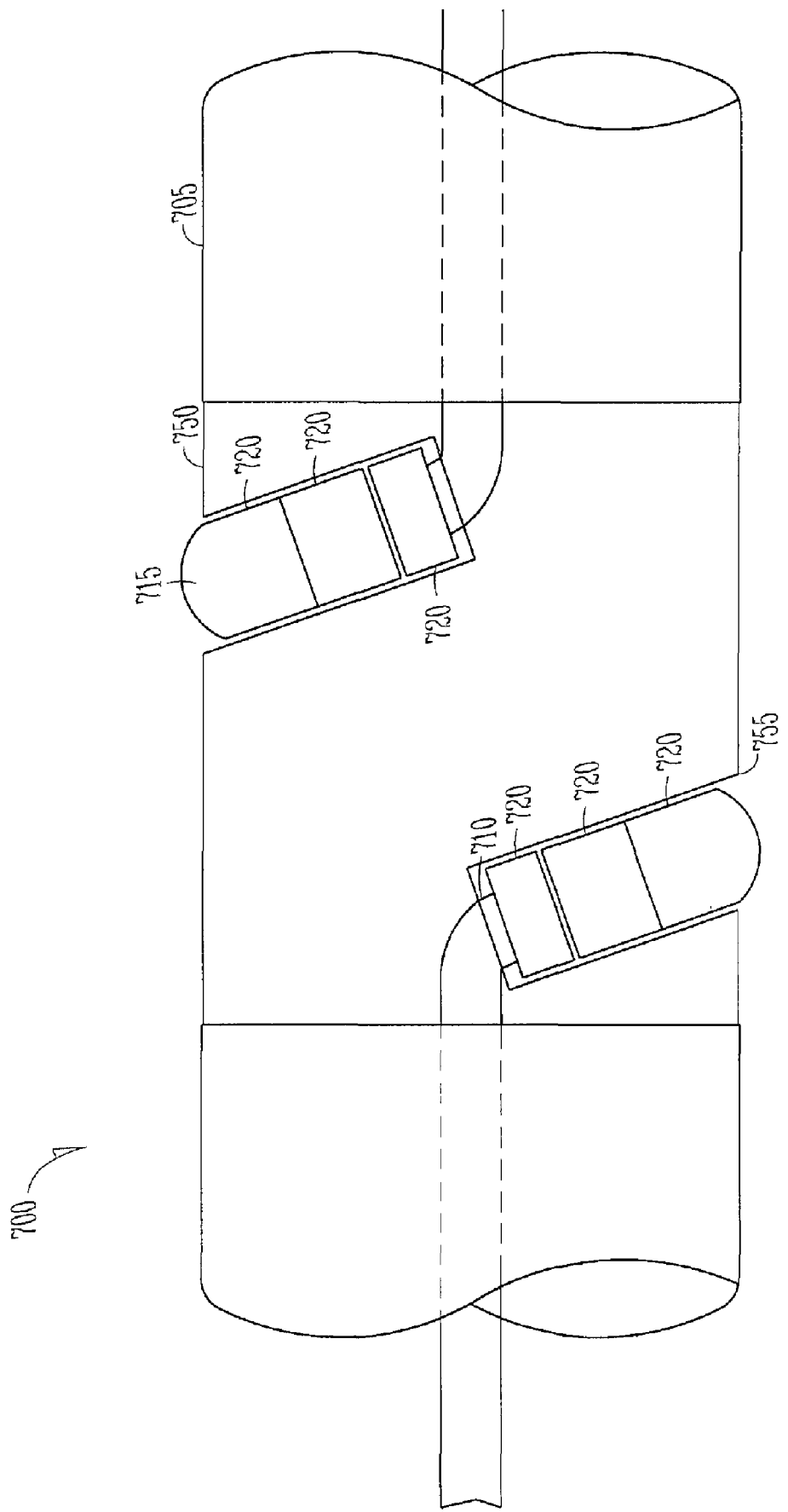

TUBULAR LEAD ELECTRODES AND METHODS

TECHNICAL FIELD

This patent document pertains generally to medical device lead assemblies, and more particularly, but not by way of limitation, to tubular lead electrodes and methods.

BACKGROUND

Medical devices such as pacers, defibrillators, and neural stimulators typically include one or more lead assemblies that carry an electrical signal to or from a location of the body. A lead assembly typically includes one or more electrodes that deliver or receive electrical therapies or signals. Many lead assemblies include sensing electrodes, for example. Lead assemblies also frequently include pacing electrodes and/or antitachyarrhythmia electrodes, such as defibrillation coils.

A lead assembly typically includes at least one conductor that extends through a lumen in a lead body and couples to an electrode. Some lead assemblies include a cuff electrode, for example.

SUMMARY

An example lead assembly includes an implantable lead body including a lumen, a conductor extending through the lumen in the lead body, and an electrode including an elongate tube expandable from a first shape to a second shape, the conductor electrically coupled to the tube. In an example, the tube is implantable in the compact shape and fixateable against a vessel wall in the predetermined expanded shape. In an example, the tube includes a shape memory alloy and the tube is expandable from the compact shape to the predetermined expanded shape by application of heat to the nitinol. In another example, the tube is formed from a spring material. In an example, the lead body is coupled to the tube, and the lead body is shapeable by expansion of the tube from the compact shape to the expanded shape. In an example, the elongate tube has an internal surface, a portion of the conductor extending into the elongate tube and electrically coupled to the internal surface.

Another example lead assembly includes an implantable lead body including at least one lumen, a conductor extending through the lumen in the lead body, and a first electrode including a first elongate tube having an internal surface, a portion of the conductor extending into the first tube and electrically coupled to the internal surface of the first tube. In an example, the lead assembly further includes a second electrode including a second elongated tube having an internal surface, a portion of the conductor extending into the second tube and electrically coupled to the internal surface of the second tube. In another example, the lead assembly further includes a second conductor extending through a lumen in the lead body, and a second electrode coupled to the second conductor, the second electrode electrically isolated from the first electrode. In an example, the tube includes a plurality of adjacent annular members, the conductor extending through the annular members. In another example, the tube includes a mesh.

Another example lead assembly includes an implantable lead body including a lumen, a conductor extending through the lumen in the lead body, and a first electrode including a first tube having an internal surface. At least a portion of the first tube forms a helix. The conductor is electrically coupled to the internal surface of the first tube. In an example, the first electrode is a defibrillation coil. In an example, the tube includes a first winding and a second winding adjacent to the first winding, the first winding connected to the second winding.

Another example lead assembly includes a lead body, an electrode coupled to the lead body and including a microcoil having an inner passage, and a conductor coupled to the lead body and extending through the inner passage of the microcoil.

An example method includes winding a tubular electrode around a mandrel, extending a conductor through a lumen in a lead body for a medical device lead assembly, and extending the conductor into the tubular electrode. In an example, winding the tubular electrode around a mandrel includes forming the tubular electrode into a helix. In an example, the method further includes welding a first winding of the helix to an adjacent winding of the helix. In an example, the method further includes bending a portion of the tubular electrode proximate an end of the tube and providing a transition for the conductor. In an example, the method further includes applying at least one of an iridium oxide coating, a titanium nitride coating, or a platinum oxide coating to the electrode.

Another example method includes extending a first conductor through a lumen in a lead body for a medical device lead assembly, forming a portion of the first conductor into a first helix, and positioning a first tubular electrode over the first helix. In an example, positioning a tubular electrode over the helix includes positioning a plurality of annular members on the helix, the plurality of annular members forming the tubular electrode, and optionally welding at least one annular member to an adjacent annular member. In another example, positioning a tubular electrode over the helix includes winding a wire around the conductor, the wire forming the tubular electrode.

BRIEF DESCRIPTION OF THE DRAWINGS

The drawings illustrate generally, by way of example, but not by way of limitation, various embodiments discussed in the present document.

FIG. 1A is an illustration of a lead assembly including an example helical tubular electrode.

FIG. 2E is an illustration of the sleeve of FIG. 2D.

FIG. 4A is a front view of another exampled helical tubular electrode.

FIG. 4B is a sectional bottom view of the example helical tubular electrode of FIG. 4A.

FIG. 4C is a side view of the example helical tubular electrode of FIG. 4A.

FIG. 6E is an illustration of an example helical tubular electrode.

FIG. 7 is an illustration of an example lead assembly including a helical conductor extending through a plurality of tubular electrode segments.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention.

Figure 1B:
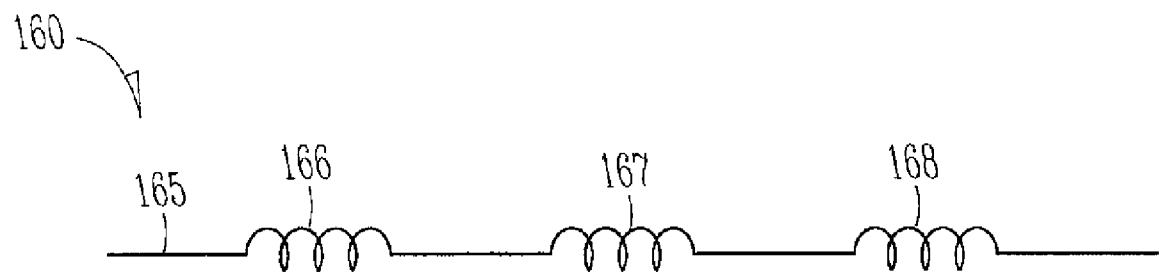
FIGS. 1B and 1C are schematic illustrations of example lead assemblies including multiple helical tubular electrodes.
Figure 1C:
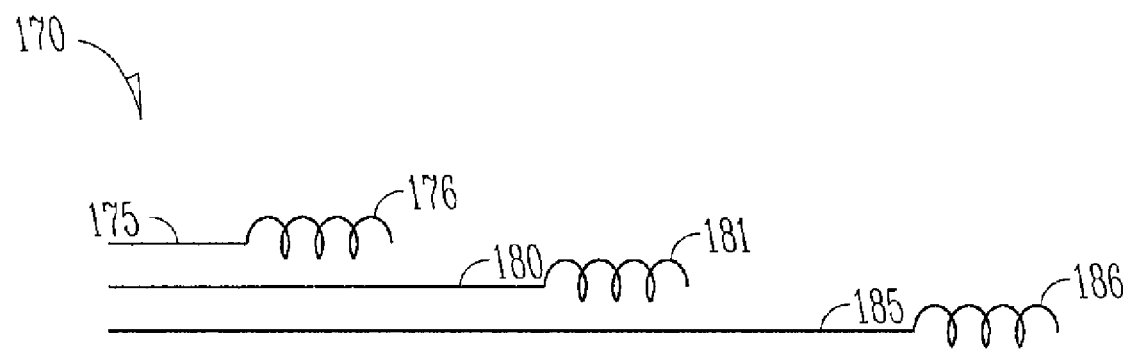
Figure 2A:
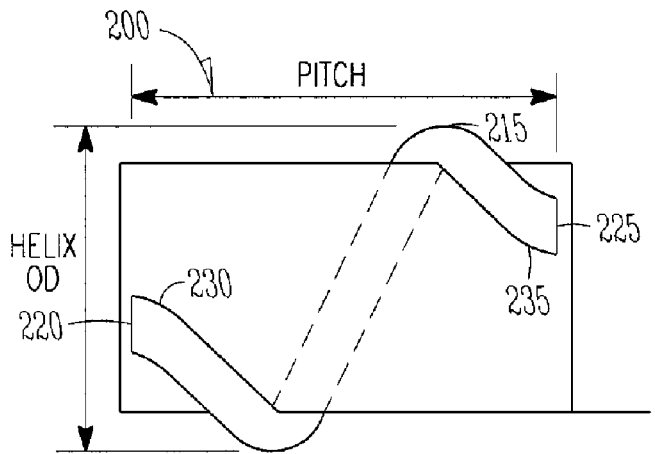
FIG. 2A is front view of an example helical tubular electrode.
Figure 8A:
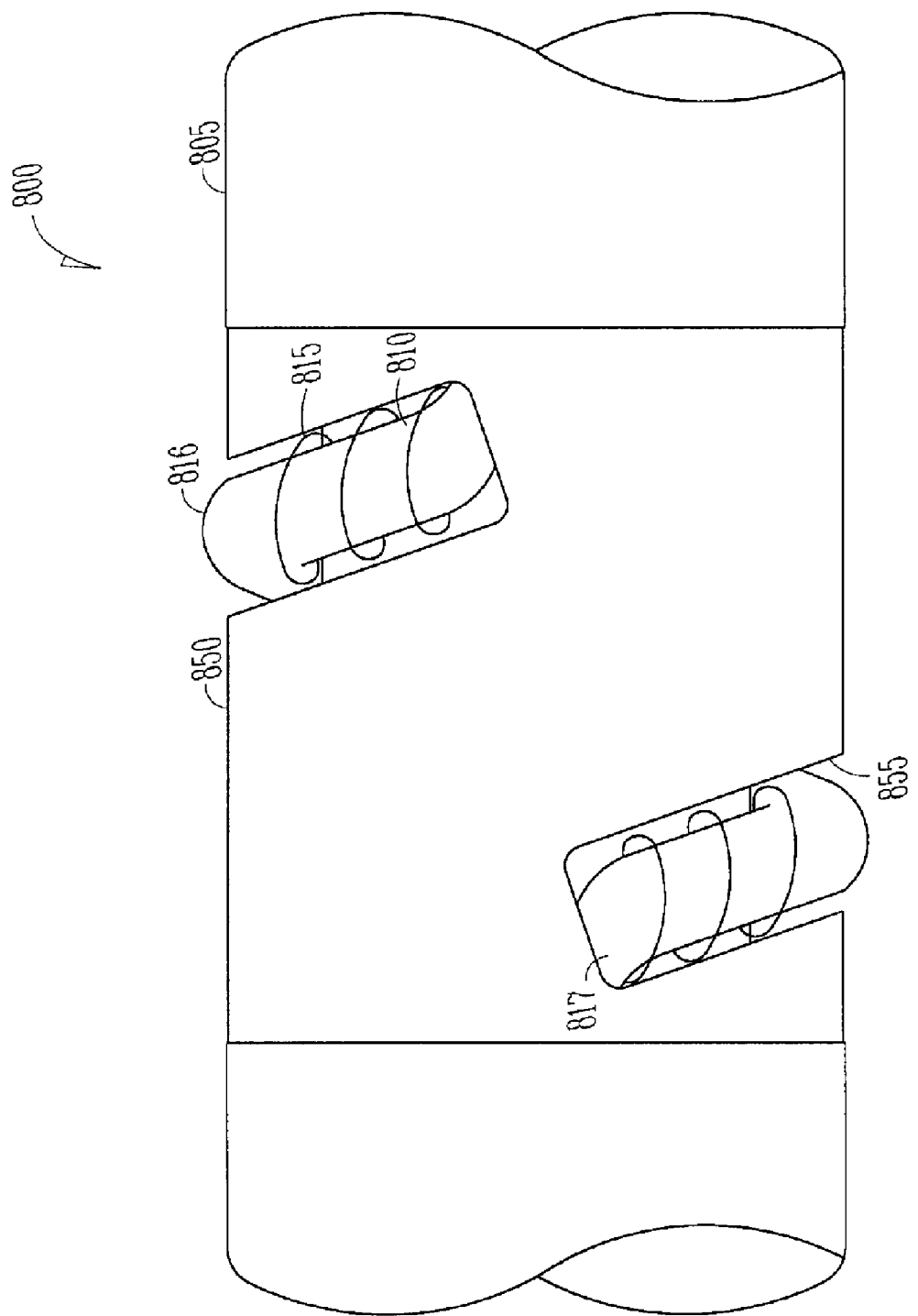
FIG. 8A is an illustration of a lead assembly including a conductor extending through a microcoil.
Figure 8B:
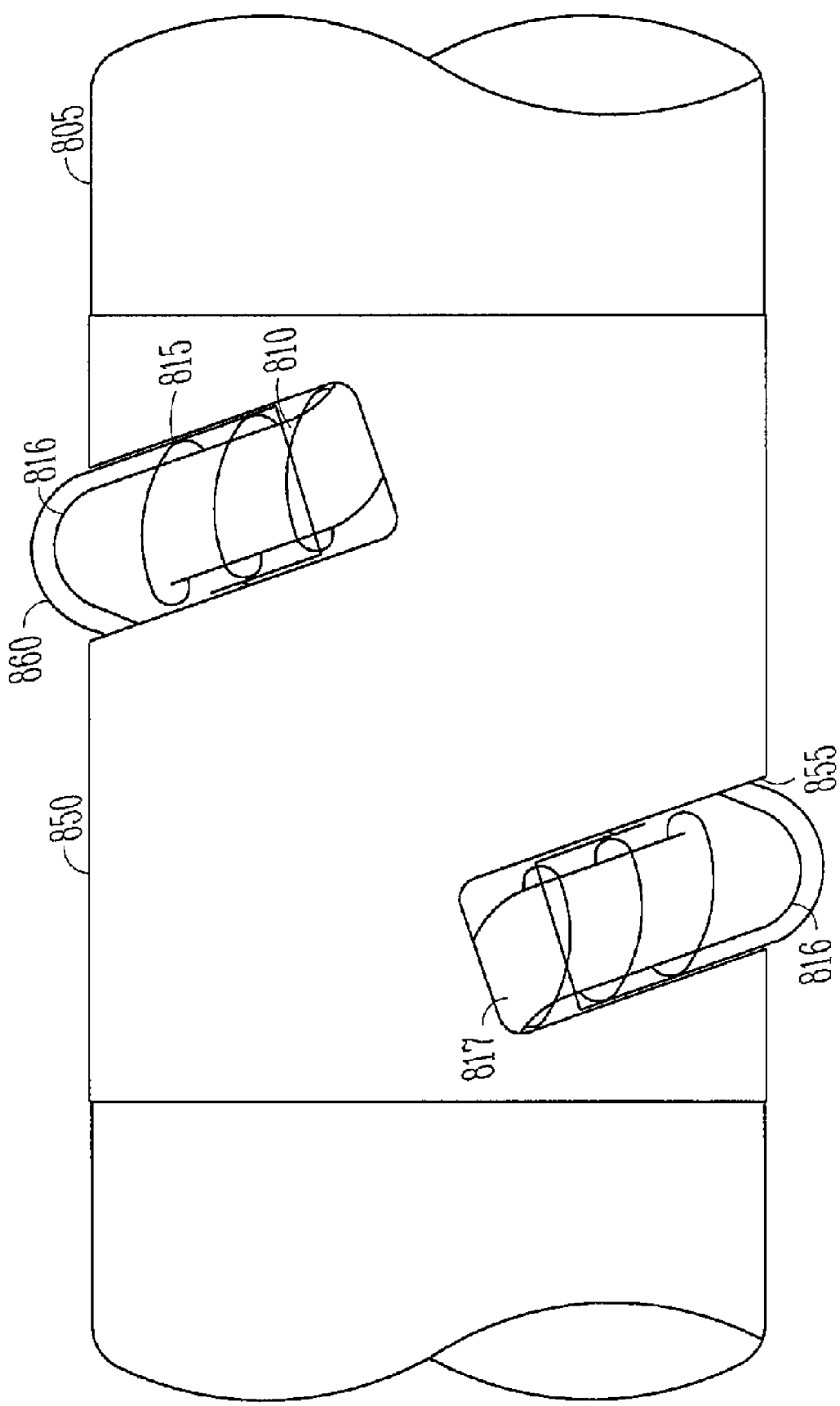
FIG. 8B is an illustration of a lead assembly including a covering on a microcoil.
Figure 8C:
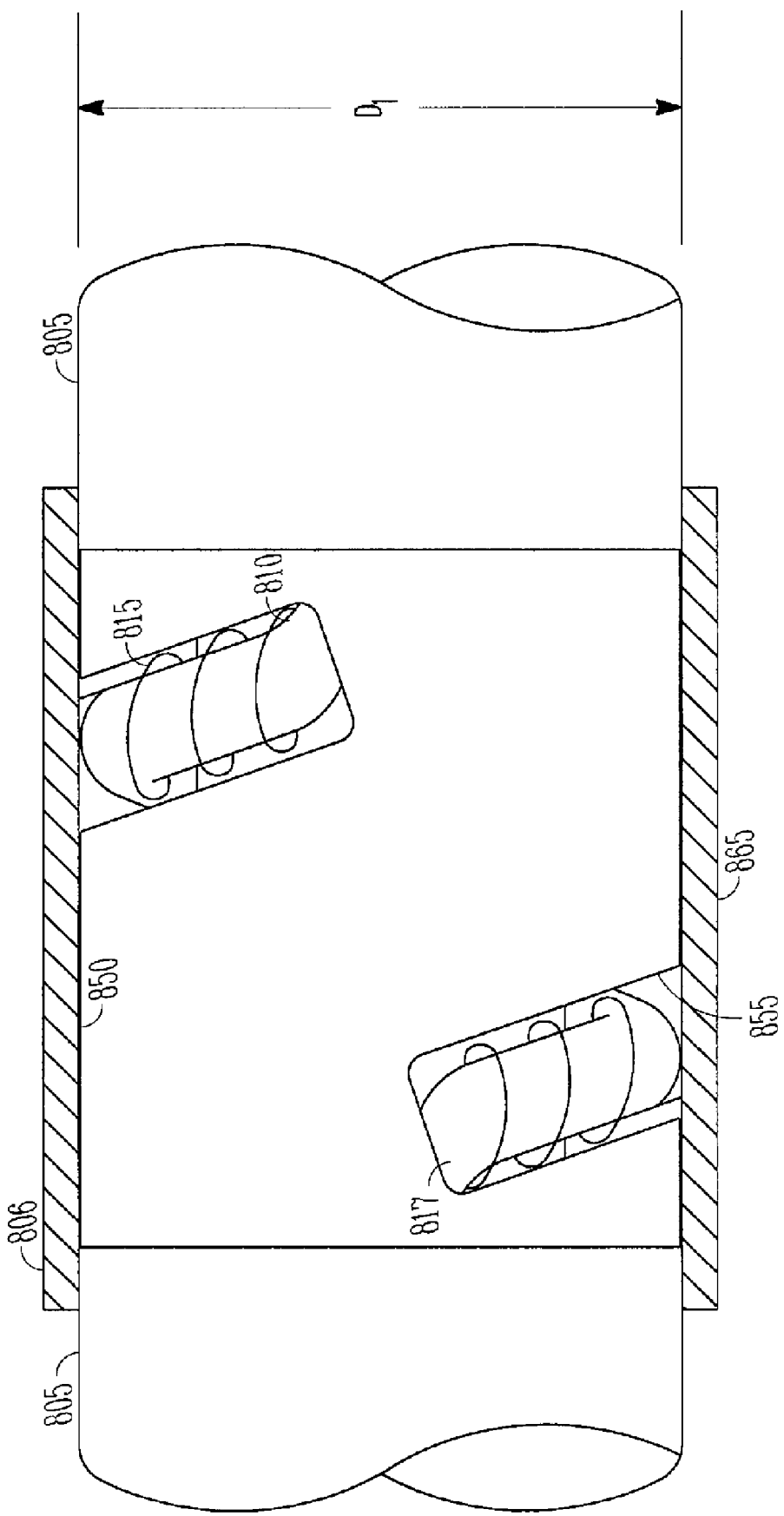
FIG. 8C is an illustration of a lead assembly including a covering over a portion of the lead assembly including a microcoil.

Various example lead assemblies include one or more tubular electrodes. In some examples the tubular electrode is helical, or formable into a helix, and the conductor extends into the tubular electrode. As used in this application, "helix" or "helical" includes, but is not limited to, any coiled or spiral-shaped member, including members of varying radius or pitch, and are not intended to be limited to a structure with a constant angular dimension. FIG. 1A shows an example where a conductor extends through a helical tubular electrode. FIGS. 1B and 1C are schematic illustrations of example lead assemblies including multiple helical tubular electrodes. FIGS. 2A-2D, 3A-3D, 4A-4D, 5A-5C, and 6A-6E show several different examples of helical electrodes and lead assemblies including helical electrodes. In some examples, windings of the helical tube are welded together, as shown in 5C and 6E. Another example lead assembly includes a conductor that extends through a plurality of segments, as shown in FIG. 7. In another example, a lead assembly includes a conductor that extends through a microcoil, as shown in FIGS. 8A-C. In some examples, a sleeve on the lead assembly includes a slot, as shown in FIGS. 2D and 2E for example. In other examples, a sleeve extends over the electrode, as shown in FIGS. 8B and 8C. In some examples, a tubular electrode is formed from a material, such as nitinol, that has a shape memory or superelastic properties. The electrodes shown in FIG. 9 and FIGS. 10A-10B, 11A-11B, and 12A-12B, for example, are returnable to a helical shape to fixate a lead assembly and/or support an electrical contact between the electrode and a vessel.

One advantage of tubular electrodes is the increased strength provided by a tube compared to a solid electrode of equal cross-sectional area. Another advantage is the ability to make a strong joint and/or a robust electrical connection between a tube and a conductor extending at least partially into the tube. An advantage of helical tubes is the ability of helical tubes to bend around tortuous bends in vascular better than similarly-sized cylindrical electrodes. Bendability can be advantageous in left side leads, for example. The bendability of tubular electrodes typically allows for use of longer tubular electrodes than cylindrical electrodes in lead assemblies. Longer electrodes can be more easily positioned in contact with myocardium or vasculature. Another advantage of tubular electrodes is that a tube has a higher surface area than a cylinder of identical diameter, because of the surface area of the inside surface of the tube. Tubes also have higher surface area than cylinders of identical cross section. Increased surface area provides, for example, increased electrical conduction capacity or electrical capacitance.

In examples, a tubular electrode has an inside diameter (ID) of about 0.001 inches to about 0.020 inches and a wall thickness of about 0.00025 inches to about 0.008 inches. Examples of helical tubes have an inner helix diameter (ID) varying from about 0.005 inches to about 0.080 inches and any pitch ranging from zero to infinity. In some examples, the pitch is about one to ten times the outer diameter of the tubular electrode.

In some examples, tubes are formed, for example, from platinum (Pt), platinum-iridium (PtIr), titanium (Ti), nickel-titanium (NiTi), tantalum (Ta), platinum-clad tantalum (PtTa), MP35N alloy, stainless steel (SST), platinum-clad titanium, a porous polymer, or a conductive polymer. Microtubes are commercially available.

In some examples, a tube has a surface that is etched, roughened, threaded, plated, polished, made from sintered porous metal, or hydrophilically coated. In an example, a tube has high aspect ratio openings, such as holes or pits, in the surface of the tube to increase the surface area. A tube may also be coated with expanded polytetrafluoroethylene (ePTFE), IROX, black platinum (PT Black), titanium nitride, an anti-inflammatory coating, or another drug coating. In an example, the tube includes or is formed from a mesh. In an example, a tube is welded or crimped, to mechanically couple and/or electrically connect the tube to a conductor. In some examples, staking, interference fits, heat bond, glue, or swage techniques are used to couple a tube to a conductor. In some examples, good conductor/tube contact is achieved in turns or helixes. In some examples, there is sufficient contact area and friction due to spring force that use of welding or other connection techniques is not needed.

Referring now to FIG. 1A, an example lead assembly 100 includes a lead body 105 that includes, for example, a tube formed from an elastomer such as silicone rubber. In an example, the lead body is implantable. A conductor 110 extends through the lead body 105. In an example, the conductor is a wire. In another example, the conductor is a cable. In another example, the conductor is a filar of a multi-filar cable. A tubular electrode 115 is electrically coupled to the conductor 110. In an example, the tubular electrode 115 forms a helix that extends around a narrowed portion 125 of the lead body. In another example, the electrode extends through a slot or lumen in the lead body.

In an example, the tubular electrode 115 has an inner diameter (ID) of about 0.007 inches and a wall thickness of about 0.002 inches. In an example, the tubular electrode 115 is formable into a helix of about 360 degrees. In other examples, the helix is greater than or less than 360 degrees. In another example, the tubular electrode 115 has an ID of about 0.004. In another example, the tube has a wall thickness of about 0.001 inches.

Referring again to FIG. 1A, the conductor 110 optionally extends into the tubular electrode 115 at a first end 130 of the electrode. The conductor 110 optionally extends through the electrode 115 and extends outwardly from a second end 135 of the electrode 115. In an example, interference and/or spring force between the conductor 110 and the tubular electrode 115 secures the electrode on the conductor. In another example, the tubular electrode 115 is crimped onto the conductor, welded to the conductor, or otherwise coupled or connected to the conductor. In an example, the tubular electrode 115 is locally crimped at one or more locations. In another example, the tubular electrode 115 is crimped along all or some of the length of the tube, for example to reduce the size of the electrode and/or change the cross-sectional shape of the electrode.

The lead assembly 100 shown in FIG. 1A also includes an optional second tubular electrode 120. In an example, the conductor 110 extends from the first electrode 115 through the lead body 105 to the second tubular electrode 120. The conductor optionally extends into a first end 140 of the second tubular electrode. In an example, the conductor 110 extends through most or all of the second electrode 120 and terminates near or at a second end 145 of the second electrode. Alternatively, the conductor extends through the second electrode 120, out of the second end 145, and extends into the lead body 105. In an example, the conductor 110 terminates in the lead body 105. In an example, an end of the conductor is glued, crimped, or heat bonded to the lead body 105. In an example, the second tubular electrode 120 is cordial with the first tubular electrode 115.

FIGS. 1B and 1C are schematic illustrations of example lead assemblies including a plurality of helical tubular electrodes. Example lead assemblies include multiple electrodes coupled to the same conductor, and/or multiple conductors coupled to electrically isolated electrodes. In FIG. 1B, example lead assembly 160 includes a conductor 165 and a plurality of helical tubular electrodes 166, 167, 168 coupled to the conductor. In FIG. 1C, example lead assembly 170 includes three conductors 175, 180, 185 and helical tubes 176, 181, 186 respectively coupled to the conductors.

In an alternative example, the first conductor does not connect with the second tubular electrode, and a second conductor couples with the second tubular electrode.

In an example, sensing is conducted through the electrode. In an example, an enhanced surface area is provide on the surface 150, 155 of the electrodes 115, 120 by etching techniques or IROX coating, for example (FIG. 1A). In another example, the tubes are formed of from porous metal. In an example, a defibrillation therapy is delivered through one or more of the electrodes 115 and 120. In another example, a pacing therapy or stimulation is delivered through one or more of the electrodes.

Figure 2B:
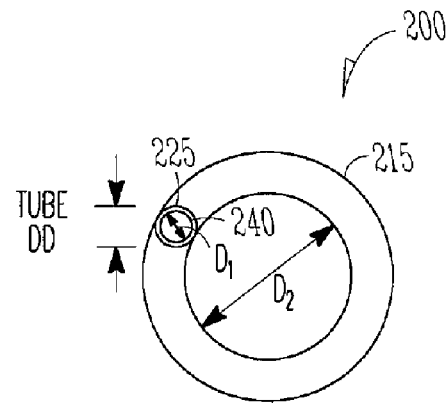
FIG. 2B is a side view of the example helical tubular electrode of FIG. 2A.

Another example electrode 200 is shown in FIGS. 2A and 2B. The electrode 200 includes a helical tube 215 having a first end 220 and a second end 225. In an example, a conductor is extended into the helical tube 215. In an example, a conductor extends into the first end 220 of the tube and out of the second end 225 of the tube. Transition portions 230, 235 of the tube near the respective first end 220 and second end 225 reduce stress risers in the conductor. In an example, the transition portions avoid abrasion of the conductor and/or reduces fatigue flex stresses. In another example, a drug-eluting compound is disposed in, or on, a portion of the tube. In an example, the drug-eluting compound reduces cell growth, inflammation and/or pacing thresholds. The tube has an inner surface 240 defining an inner diameter D1, shown in FIG. 2B. The helical tube 215 defines an inner diameter D2 of the helix.

Figure 2C:
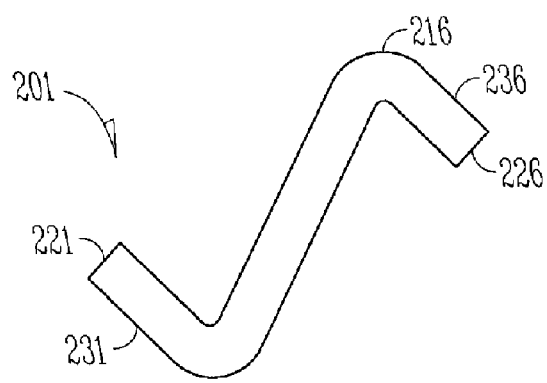
FIG. 2C is a front view of another example helical tubular electrode.
Figure 2D:
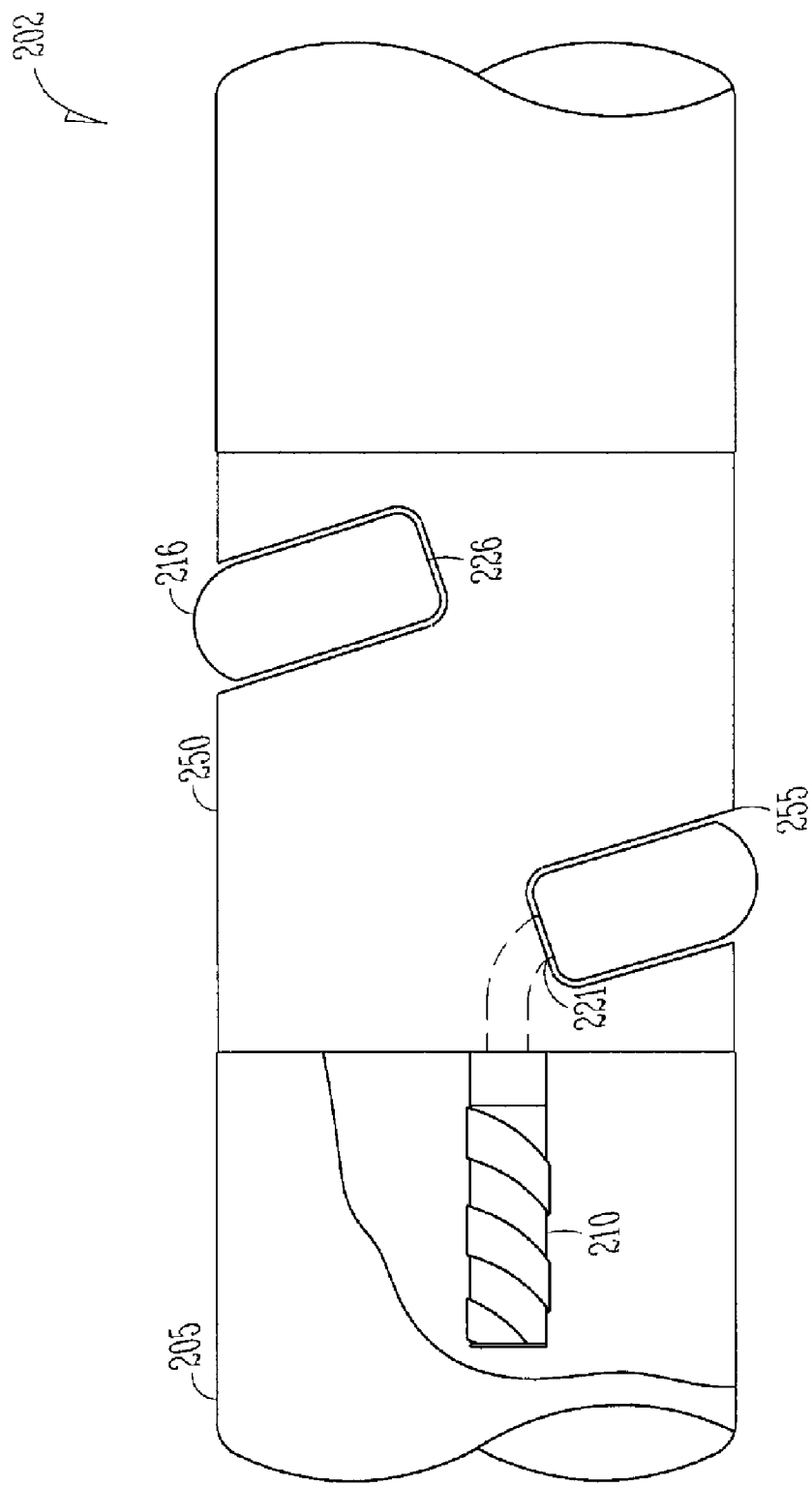
FIG. 2D is an illustration of a lead assembly including the example helical tubular electrode of FIG. 2C and a sleeve.

FIG. 2C illustrates another example electrode 201 including a tube 216, in which portions 231, 236 near first and second ends 221, 226 of the tube extend at approximated 45 degrees from horizontal. The ends 221, 226 of the tube are approximately perpendicular to the portions 231, 236. In an example, the helical tube has a pitch of about five to six times the outside diameter (OD) of the tube, a helix outer diameter of about five to six times the OD of the tube, and a tube wall thickness of about one-fifth the OD of the tube. In an example, the tube has an OD of about 0.011 inches, a pitch of about 0.060 inches, a helix outer diameter of about 0.053 inches, and a wall thickness of about 0.002 inches. In an example, the length, pitch, or other dimensions of the tube are selected to provide performance for an intended function of the electrode, i.e. shocking, defibrillation, pacing, sensing, neural stimulation, or some combination thereof.

FIG. 2D shows an example lead assembly 202 that includes the helical tube 216, a lead body 205, a sleeve 250 having a helix-shaped slot 255, and a conductor 210 extending through the tube. The conductor 210 enters the first end 221 of the tube 216, extends through the tube, and exits the tube at the second end 226. A side view of the sleeve 250 is shown in FIG. 2E. In an example, the slot 255 in the sleeve 250 allows a portion of the lead assembly to be insulated while exposing the electrode to allow delivery of an electrical signal to a blood vessel or other tissue near the electrode. In an example, the lead assembly 202 is isodiametric, and the electrode has an outer surface that has approximately the same outside diameter as the sleeve 255 and lead body 205. In another example, the electrode has an outer diameter that is larger than the outer diameter of the lead body and/or sleeve. In an example, the sleeve is drug-eluting, or a drug-eluting material is disposed on or in the sleeve.

Figure 3C:
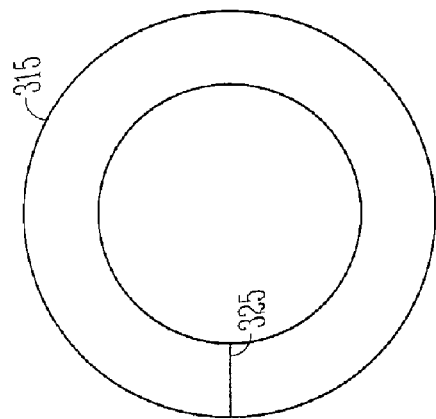
FIG. 3C is a side view of the helical tubular electrode of FIG. 3A.
Figure 3A:
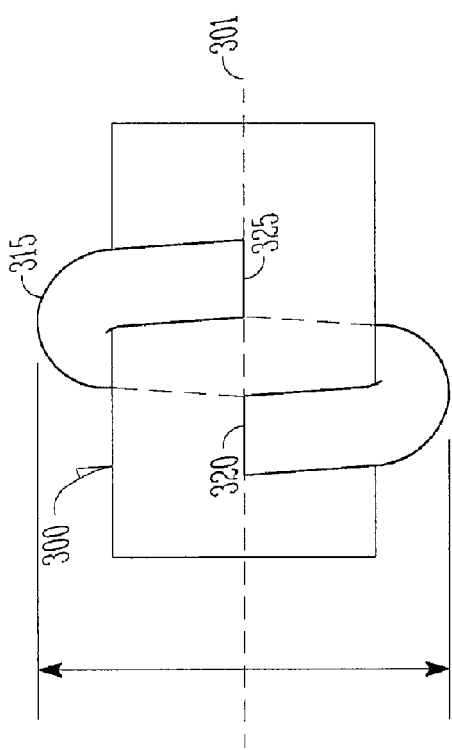
FIG. 3A is a front view of another example helical tubular electrode.
Figure 3B:
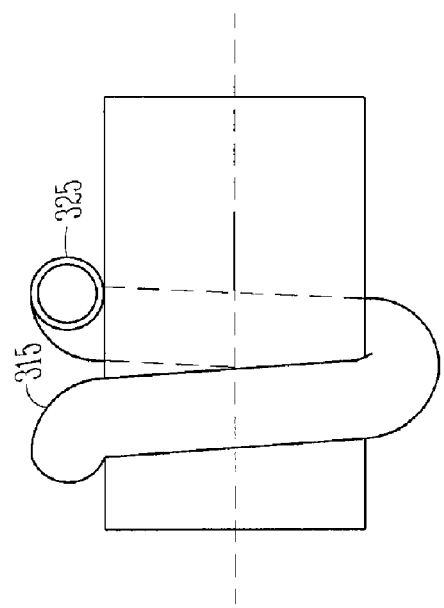
FIG. 3B is a bottom view of the helical tubular electrode of FIG. 3A.

Another example electrode 300 is shown in FIGS. 3A-3C. The electrode 300 includes a tube 315 having a first end 320 and a second end 325. In an example, the first and second ends 320, 325 are approximately perpendicular to the axis 301 of the helix. In an example, the tube has a pitch of about two times the outer diameter (OD) of the tube. In an example, the OD of the tube is about 0.011 inches, the tube wall thickness is about 0.002 inches, and the outer diameter of the helix is about 0.053 inches.

Figure 3D:
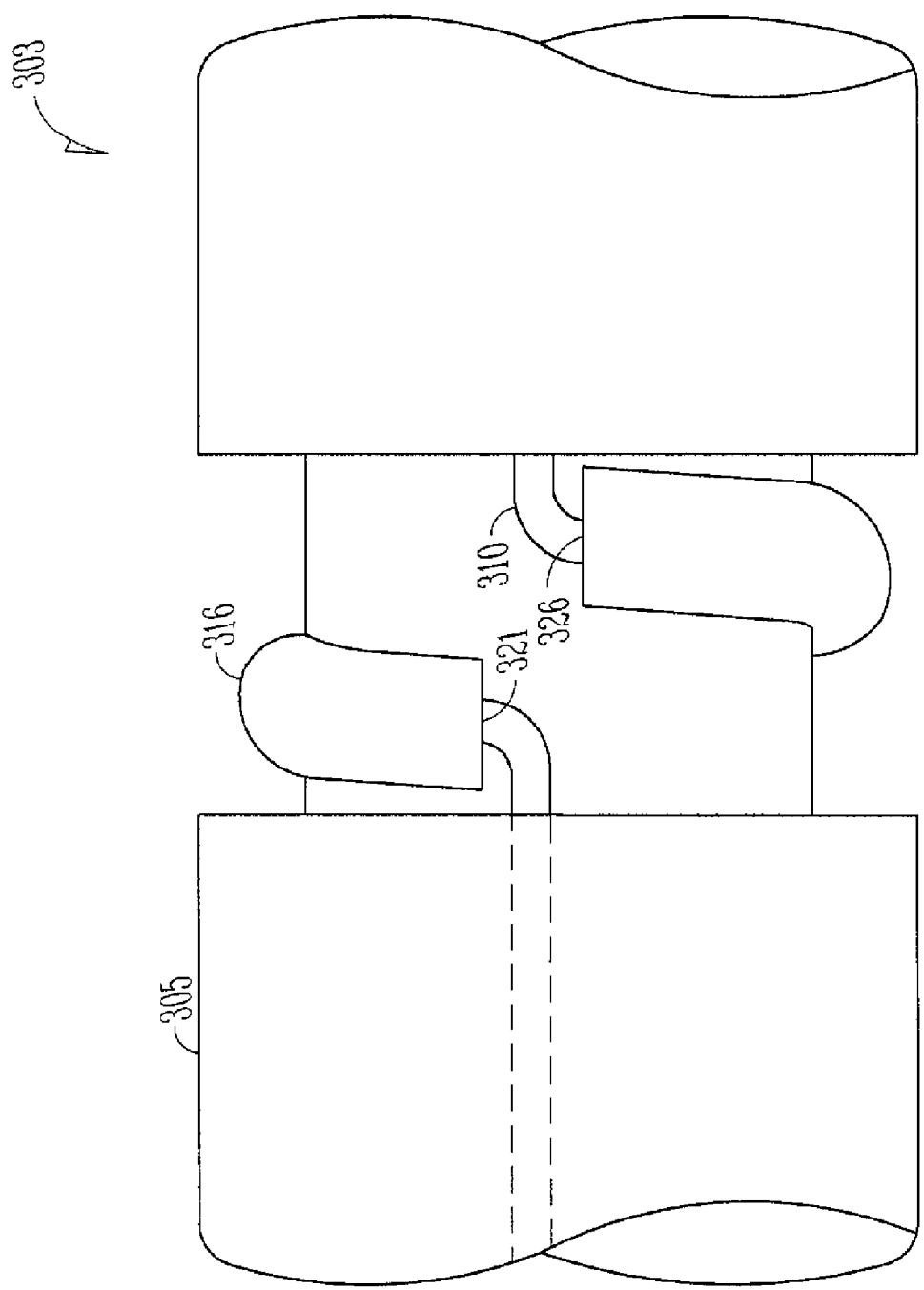
FIG. 3D is an illustration of a lead assembly including the example helical tubular electrode of FIG. 3A.

FIG. 3D illustrates another example lead assembly 303 including a tube 316. In the example shown in FIG. 3D, the helical tube 316 has a pitch that is approximately the same as the outer diameter of the tube. In an example, the OD of the tube is about 0.011 inches. A conductor 310 extends through a lead body 305, enters a first end 321 of the tube, and exits a second end 326 of the tube.

Figure 4D:
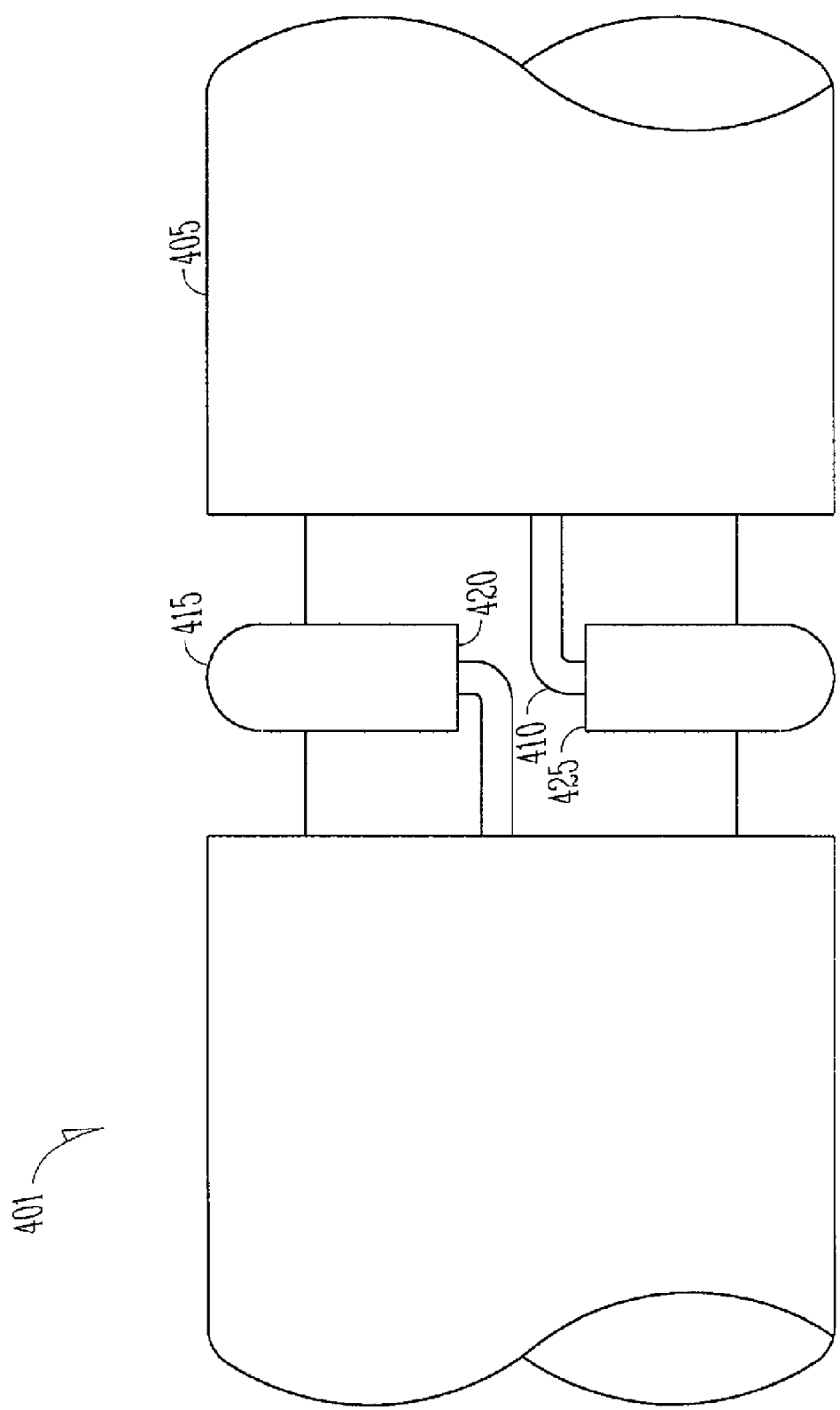
FIG. 4D is an illustration of a lead assembly including the helical tubular electrode of FIG. 4A.

FIGS. 4A-4C illustrate another example electrode 400 including a tube 415 having a pitch of about zero, i.e. the tube extends in a circle. The tube has a first end 420 and a second end 425. In an example, the first end 420 and second end 425 are coplanar. In an example, the tube follows an arc of a circle, i.e. the pitch of the tube is zero. FIG. 4B shows a sectional view of the tube 415. The tube has an inner surface 440 defining an inner diameter (ID). In an example, the ID is about 0.007 inches and the outer diameter (OD) of the tube is about 0.011 inches. FIG. 4C is a side view of the tube 415. In an example, tube 415 extends circularly at a diameter of about 0.053 inches. FIG. 4D illustrates an example lead assembly 401 including the helical tube 415 shown in FIGS. 4A-4C. A conductor 410 extends through a lead body 405, into the first end 420 of the tube 415, through the tube, and out of the second end 425 of the tube.

Figure 5B:
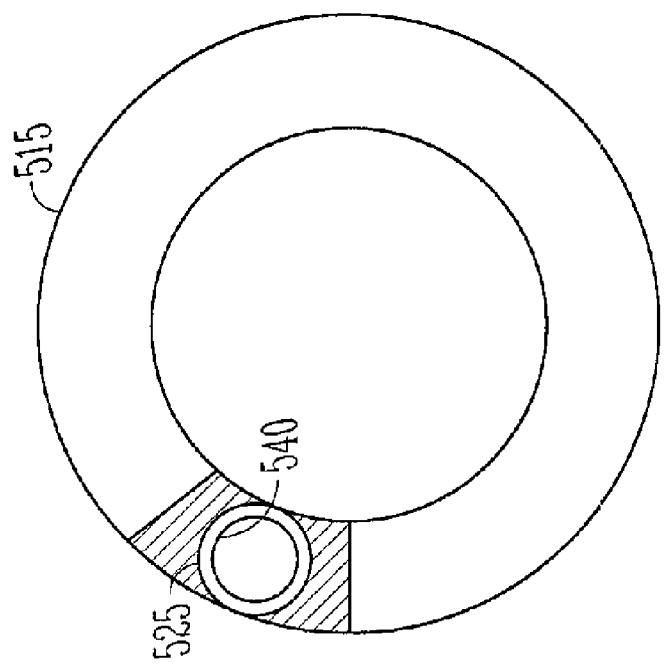
FIG. 5B is a side view of the example helical tubular electrode of FIG. 5A.
Figure 5A:
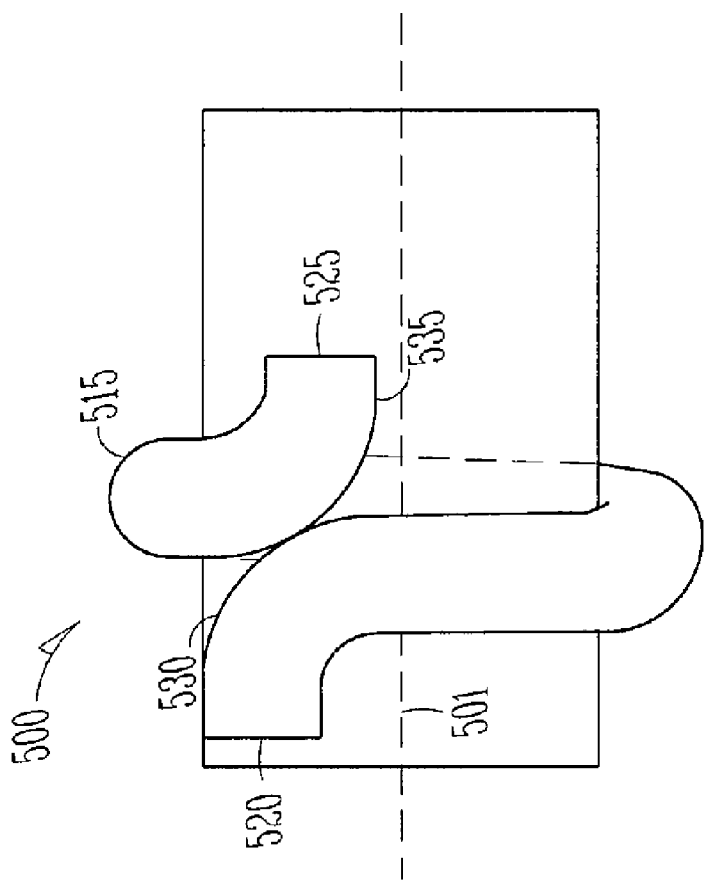
FIG. 5A is a front view of an example helical tubular electrode.

Referring now to FIGS. 5A-5B, another example electrode 500 includes a tube 515 having a first end 520 and a second end 525. First and second transition portions 530, 535 of the tube 515 near the respective first and second ends 520, 525 bend toward the helix axis 501. In an example, the transition portions 530, 535 reduce stress risers in a conductor extending into or through the tube. In an example, the first and second transition portions 530, 535 touch each other. In an example, the first transition portion 530 is connected to the second transition portion 535, for example with a weld. Referring now to FIG. 5B, an internal surface 540 of the tube 515 defines an inner diameter (ID) of the tube. In an example, the ID of the tube is about 0.007 inches and the wall thickness of the tube is about 0.002 inches. In an example, the outer diameter of the helix is about 0.053 inches.

Figure 5C:
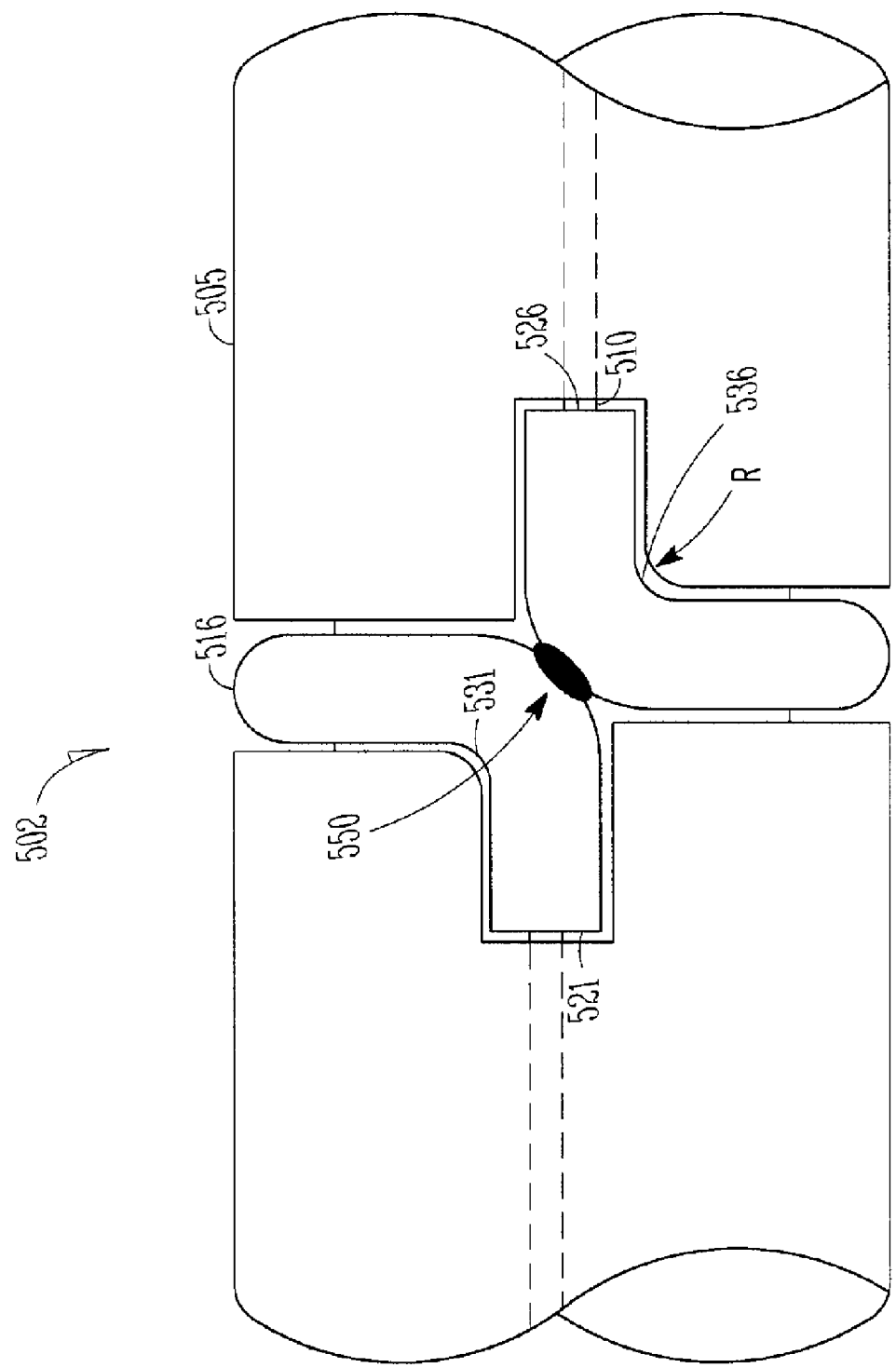
FIG. 5C is an illustration of a lead assembly including an example helical tubular electrode.

FIG. 5C shows an example lead assembly 502 that includes a tube 516 having first and second transition portions 531, 536 connected together. In an example, the transition portions 531, 536 are connected with a weld 550. In an example, a conductor 510 extends through the lead body 505 and into a first end 521 of the tube 516. In an example, the conductor 510 extends through the tube 516 and out of a second end 526 of the tube. In an example, the weld 550 prevents axial stretching of the tube 516.

Figure 6B:
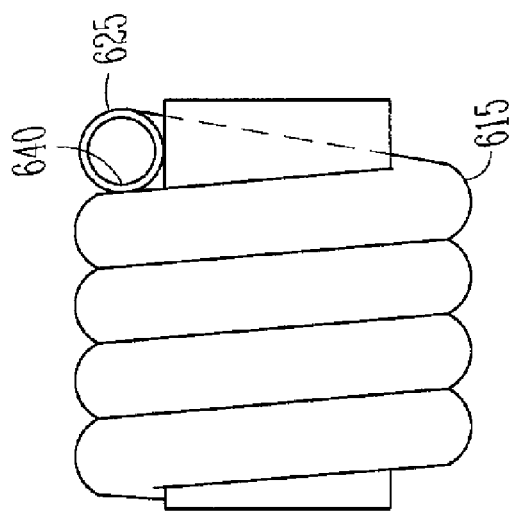
FIG. 6B is a bottom view of the example helical tubular electrode of FIG. 6A.
Figure 6A:
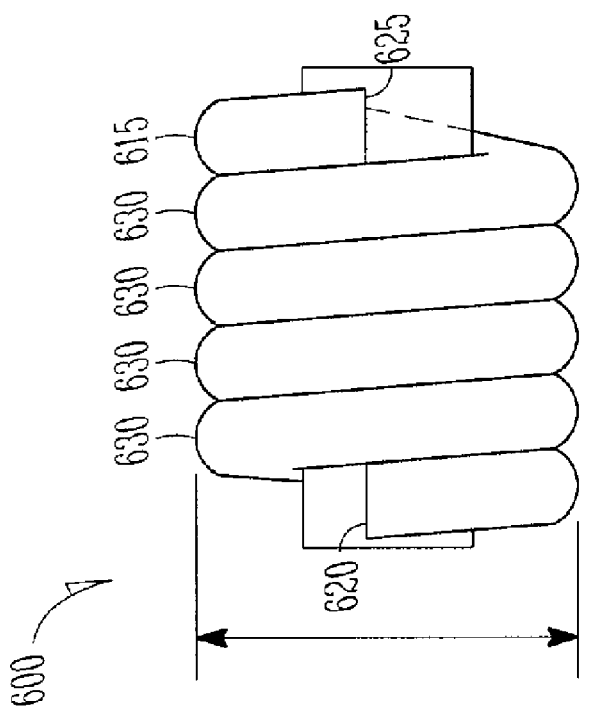
FIG. 6A is a front view of another example helical tubular electrode.

Referring now to FIGS. 6A-6B, another example electrode 600 includes a tube 615 having several windings. As shown in FIG. 6A, the tube 615 has a first end 620, a plurality of windings 630, and a second end 625. In an example, the tube 615 winds through approximately five turns, i.e. through about 1800 degrees. In an example, two or more adjacent windings touch each other, and are optionally welded together. FIG. 6B shows an internal surface 640 of the tube that defines an inner diameter (ID) of the tube. In an example, the ID of the tube 615 is about 0.007 inches and the tube has a wall thickness of about 0.002 inches.

Figure 6D:
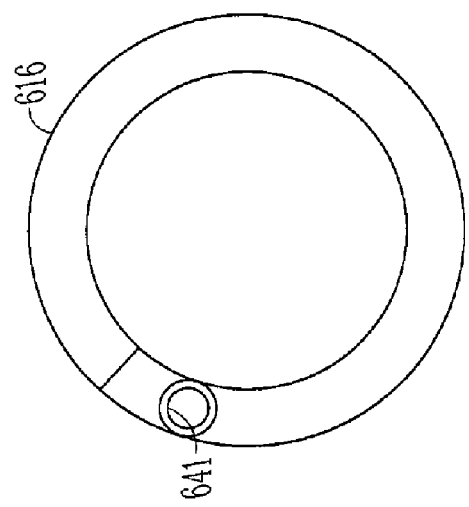
FIG. 6D is a side view of the example helical tubular electrode of FIG. 6C.
Figure 6C:
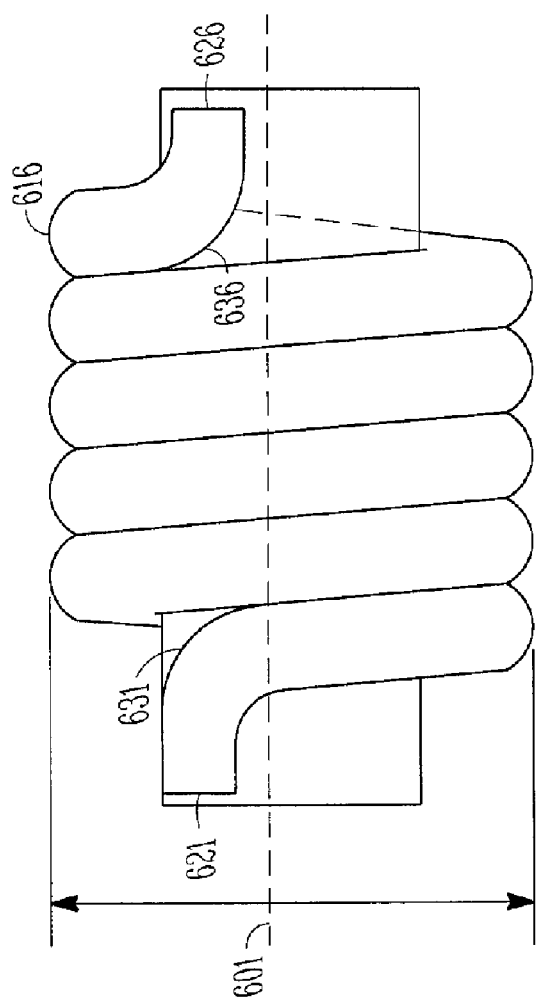
FIG. 6C is a front view of another example helical tubular electrode.

FIG. 6C illustrates another example electrode including a multi-winding tube 616 that has first and second transition portions 631, 636 near the respective first and second ends 621, 626 of the tube. In an example, the transition portions 631, 636 bend toward the axis 601 of the helical tube 616.

FIG. 6D shows an end view that shows an inner surface 641 that defines an inner diameter of the tube.

FIG. 6E illustrates an example lead assembly that includes a lead body 605, a helical tubular electrode 617, and a conductor 610 extending through the lead body and the helical tubular electrode 617. The conductor 610 extends into a first end 622 of the electrode and out a second end 627 of the electrode. The conductor includes a bend 611 that turns into the tubular electrode 617. The electrode 617 includes a plurality of welds 650 that connect adjacent windings of the helix. In an example, the welds prevent axial stretching of the electrode.

Referring now to FIG. 7, in another example, a lead assembly 700 includes a lead body 705, and a conductor 710 extending through the lead body and through and a plurality of annular members 720, such as tubular segments. In an example, the tubular segments are positioned together on the conductor, i.e. arranged in a "string-beads" or "box-car" configuration on the lead assembly. In an example, the annular members 720 touch adjacent segments, and/or are connected to adjacent segments. In an example, the annular members 720 are straight tubes. In another example, the annular members 720 are torroidal. In an example, some or all of the annular members 720 are crimped or welded on the conductor. In another example, the annular members extend only part way around the conductor, for example in a "C" shape.

In an example, the plurality of annular members 720 together form an electrode 715. In an example, the lead assembly includes a sleeve 750 including a slot 755 that follows the shape of the electrode 715 formed by the conductor 710 and annular members 720. In an example, the annular members 720 form a helical electrode and the sleeve includes a helical slot, as shown in FIG. 7. In an example, the annular members 720 reside in the slot and, in combination with the outer surface of the lead body, provide an approximately isodiametric surface.

Referring now to FIG. 8A, another example lead assembly 800 includes a lead body 805 and a conductor 810 extending along and/or through the lead body. At least a portion 816 of the conductor 810 extends in a helix. The helical portion 816 of the conductor extends through an inner diameter of a microcoil 815. A microcoil is a coil approximately half the diameter of the lead, or smaller. In an example, the microcoil fits over another conductor or is attached to another conductor to form an electrode or fixation device. In an example, the microcoil 815 includes a wire that extends helically around the conductor 810. In an example, the wire has a diameter of about 0.00025 inch to 0.005 inch and is formed in a coil having an inside diameter of about 0.002 inch to 0.015 inch. In an example, the microcoil has a constant pitch and constant inner diameter. In an alternative example, the helix varies in pitch and/or diameter. The microcoil 815 is electrically coupled to the conductor, unless it is used exclusively for fixation. In an example, the microcoil 815 is welded, crimped, or otherwise connected to the conductor 810. In another example, the spring force of the microcoil is sufficient for electrical coupling. In an example, an end 817 of the microcoil are welded or otherwise connected to the conductor 810 to prevent tissue abrasion. In an example, the lead assembly 800 also includes a sleeve 850 that has a slot 855 that follows the shape of the helical portion 816 of the conductor. In an example, the sleeve 850 is isodiametric with the lead body 805.

Referring now to FIG. 8B, in an example, the lead assembly includes a covering 860 that extends over the microcoil 815. In an example, the covering 860 is a sleeve. In another example, the covering 860 is a coating. In an example, the covering prevents or reduces tissue ingrowth near the microcoil.

In an example, the covering 860 includes a porous material, such as expanded polytetrafluoroethylene (ePTFE), expanded ultra high molecular weight polyethylene (eUHM-WPE), or another expanded or porous polymer. In an example, the covering includes nanoholes. In an example, nanoholes in a polymer covering are made by alpha particle bombardment followed by etching away the polymer section that the alpha particle tracked through the polymer film. In an example, the covering includes a material that is drug-eluting. In other examples, a covering is applied or extended on or over other types of electrodes, such as the electrodes shown in FIGS. 1-7.

In another example, illustrated in FIG. 8C, a covering 865 extends over the microcoil 815 as well as the lead body 805, and/or the sleeve 850. In an example, the covering 865 has an inner diameter that is approximately the same as an outer diameter D1 of a helix formed by the conductor and microcoil. In an example, the covering 865 extends over the sleeve 850 and electrode 815. In an example, a portion 806 of the covering also extends over a portion of the lead body 805.

Figure 9A:
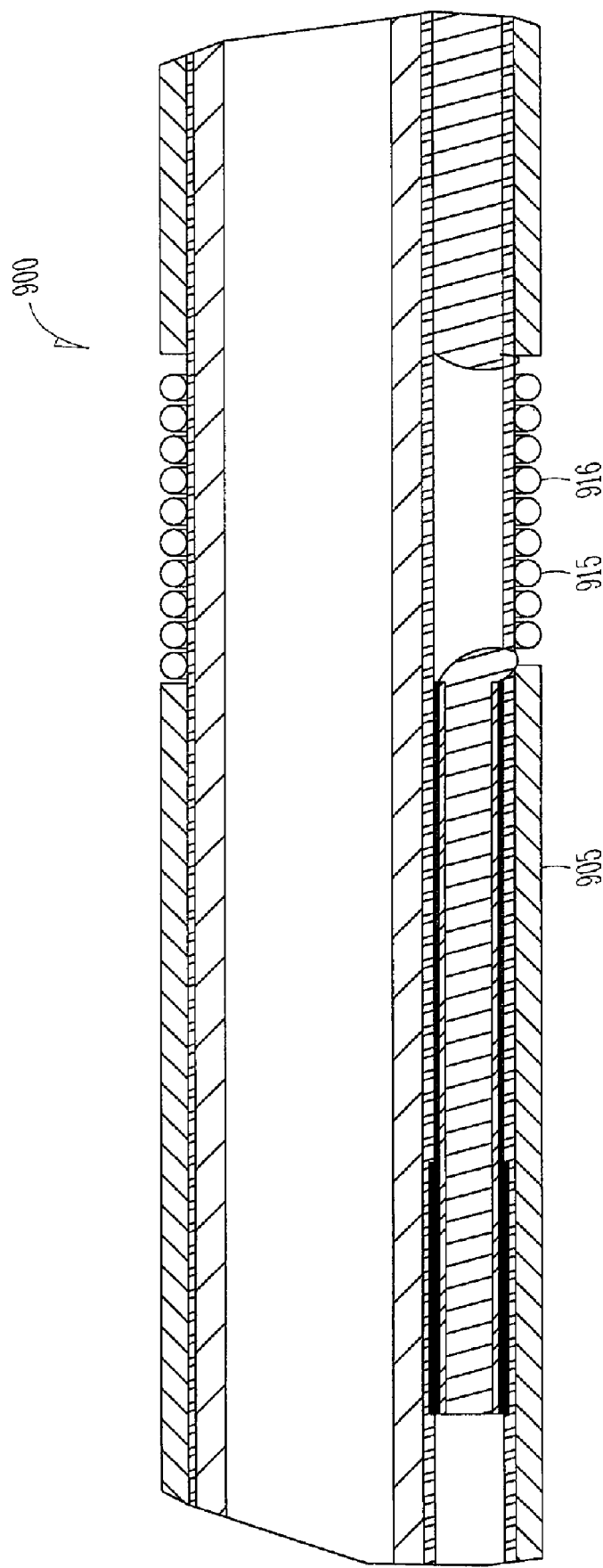
FIG. 9A is a cross-sectional illustration of another example of a lead assembly.
Figure 9B:
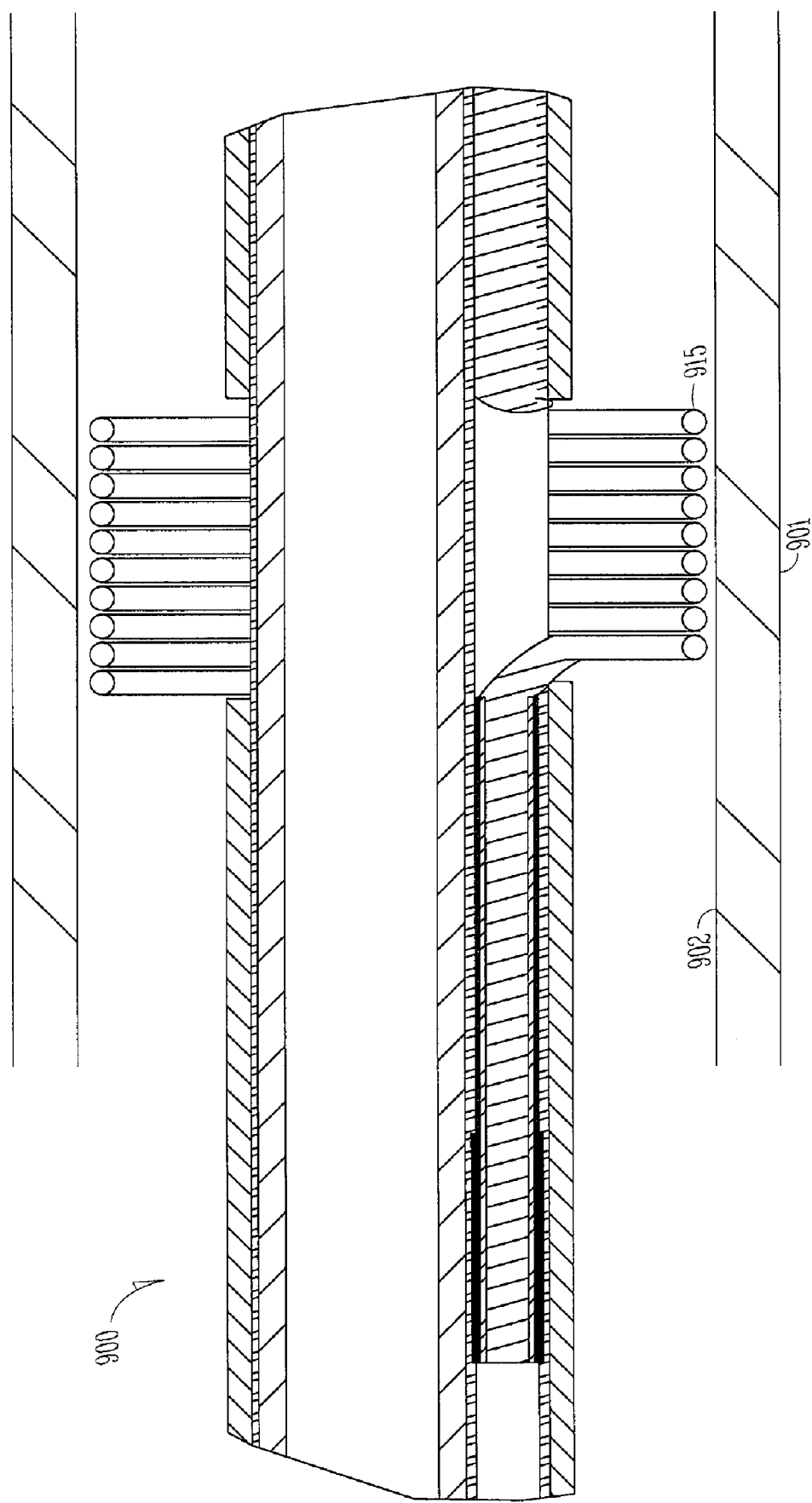
FIG. 9B is a cross-sectional illustration of another example of the lead assembly of FIG. 9A in an expanded configuration in a vessel.

Referring now to FIGS. 9A-9B, in another example, a lead assembly 900 includes a lead body 905 and an expandable helical electrode 915. In an example, the expandable electrode 915 includes a helical tube 916. In another example, the expandable electrode is solid. In an example, the expandable helical electrode is formed from an elastic shape-memory alloy, such as nitinol (Nickel Titanium Naval Ordnance Laboratory alloy). Nitinol is returnable to a shape such as a helix with application of heat. FIG. 9A shows the electrode 915 in a compact shape. FIG. 9B shows the electrode in an expanded shape. In an example, the electrode 915 is expandable against an inner surface 902 of a vessel 901 to establish electrical contact with the vessel and/or fixate the lead assembly 900 in the vessel.

Figure 10A:
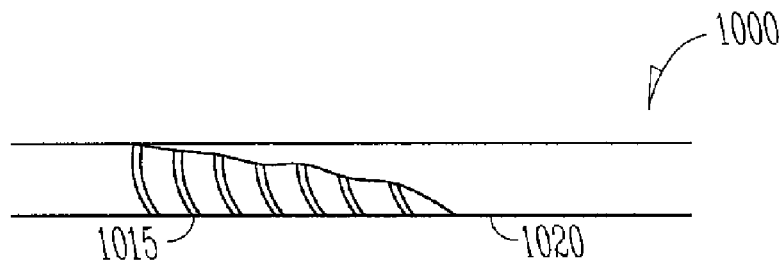
FIG. 10A is an illustration of a lead assembly including a helical tube and a sleeve.
Figure 10B:
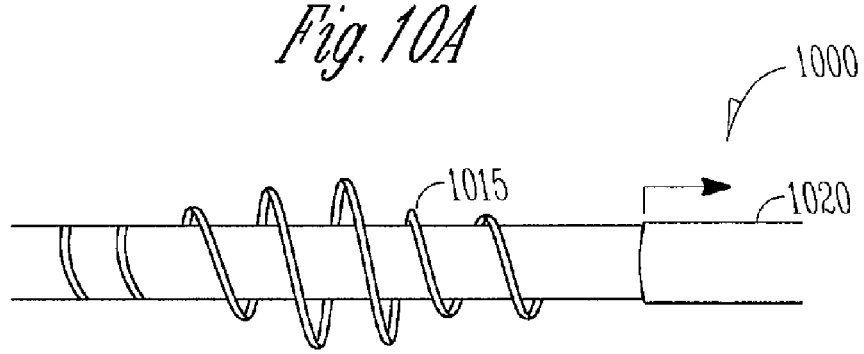
FIG. 10B is an illustration of the lead assembly of FIG. 10A with the sleeve pulled off the helical tube.

Another example expandable electrode 1015 is illustrated in FIGS. 10A-10B. In an example, the expandable electrode 1015 includes a spring material, such as a metallic spring. A lead assembly 1000 includes the expandable electrode 1015 and a sleeve 1020. The sleeve 1020 holds the electrode 1015 in a contracted configuration, as shown in FIG. 10A. The sleeve is shown partially cut-away to show the electrode inside the sleeve. In an example, the lead assembly 1000 is isodiametric when the electrode is in the contracted configuration. When the sleeve is pulled off the electrode 1015, the electrode expands to an expanded configuration, as shown in FIG. 10B. In an example, the electrode expands to fixate the lead assembly in a vessel, and/or to establish electrical contact with a vessel for delivery of a therapy. In an example, the sleeve includes a drug-eluting compound. In an example, a drug is coated on the sleeve or mixed into the sleeve. In an example, the drug minimizes inflammation and/or cell growth and/or keeps pacing thresholds low.

Figure 11A:
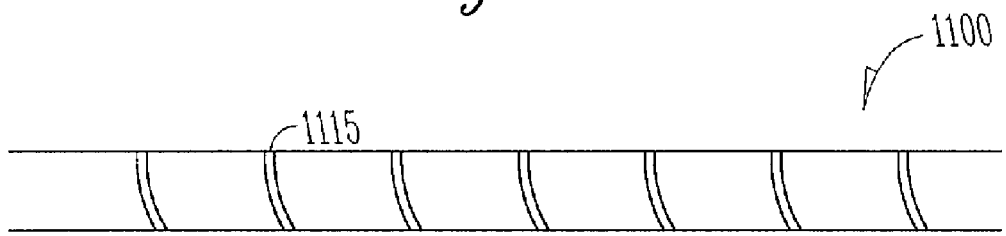
FIG. 11A is an illustration of a lead assembly including a helical tube, showing the lead assembly in a straight configuration.
Figure 11B:
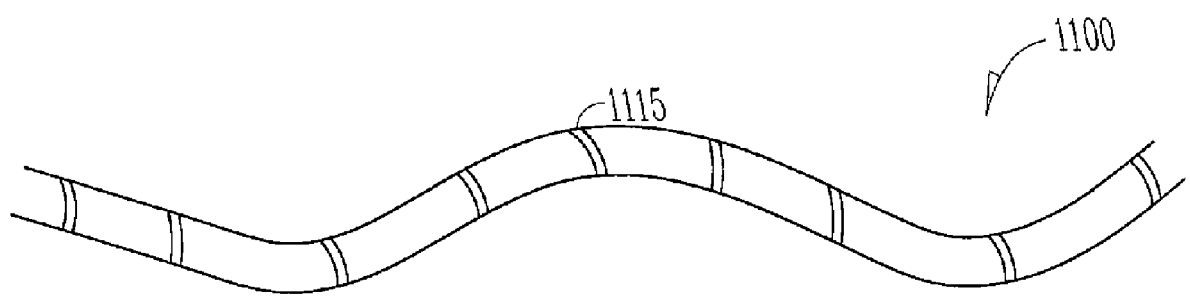
FIG. 11B is an illustration of a lead assembly including a helical tube, showing the lead assembly in a helical configuration.

FIGS. 11A-11B illustrate another example lead assembly. The lead assembly 1100 includes an electrode 1115 that is formed from a shape-memory material, such as nitinol. The electrode 1115 is formable into a different shape, for example by application of heat to a nitinol electrode. In an example, the electrode 1115 is wound around the lead assembly 1100, and the electrode and lead assembly are formable into a helix, as shown in FIG. 11B. In another example, the electrode 1115 is wound into a sinusoid or other 2-dimensional or 3-dimensional shape to provide electrical contact and/or fixation. In an example, a lead assembly includes two or more shape-memory tubular electrodes.

Figure 12A:
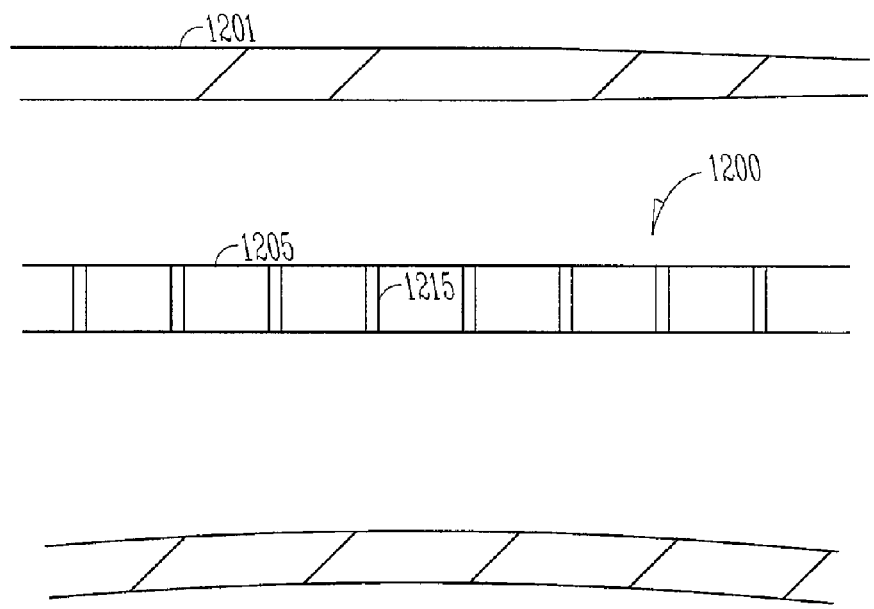
FIG. 12A is an illustration of another example lead assembly in a straight configuration in a vessel.
Figure 12B:
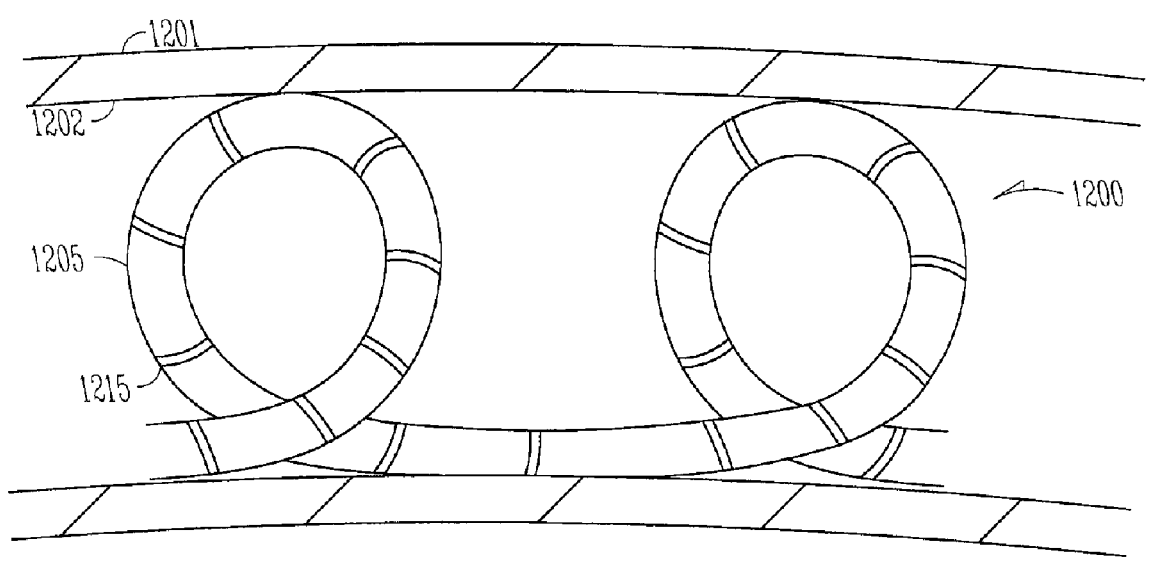
FIG. 12B is an illustration of the lead assembly of FIG. 12A in a helical configuration in a vessel.

FIGS. 12A-12B illustrate a lead assembly 1200 in a blood vessel 1201. The lead assembly includes a lead body 1205 and an electrode 1215 formed from a shape-memory material, such as nitinol. The lead assembly 1200 and electrode 1215 are shapeable into a helix by application of heat to the nitinol electrode. As shown in FIG. 12B, the lead assembly 1200 and electrode 1215 are shapeable to fixate the lead assembly in a vessel and/or to establish electrical contact between the electrode and an inner surface 1202 of the blood vessel. In an example, the lead assembly 1200 does not occlude the vessel 1201 when the lead assembly is in the helical shape. Any of the tubular electrodes disclosed in this application, including the electrode 1215 shown in FIGS. 12A-12B, can include a drug-eluting compound disposed in or on the electrode.

Figure 13:
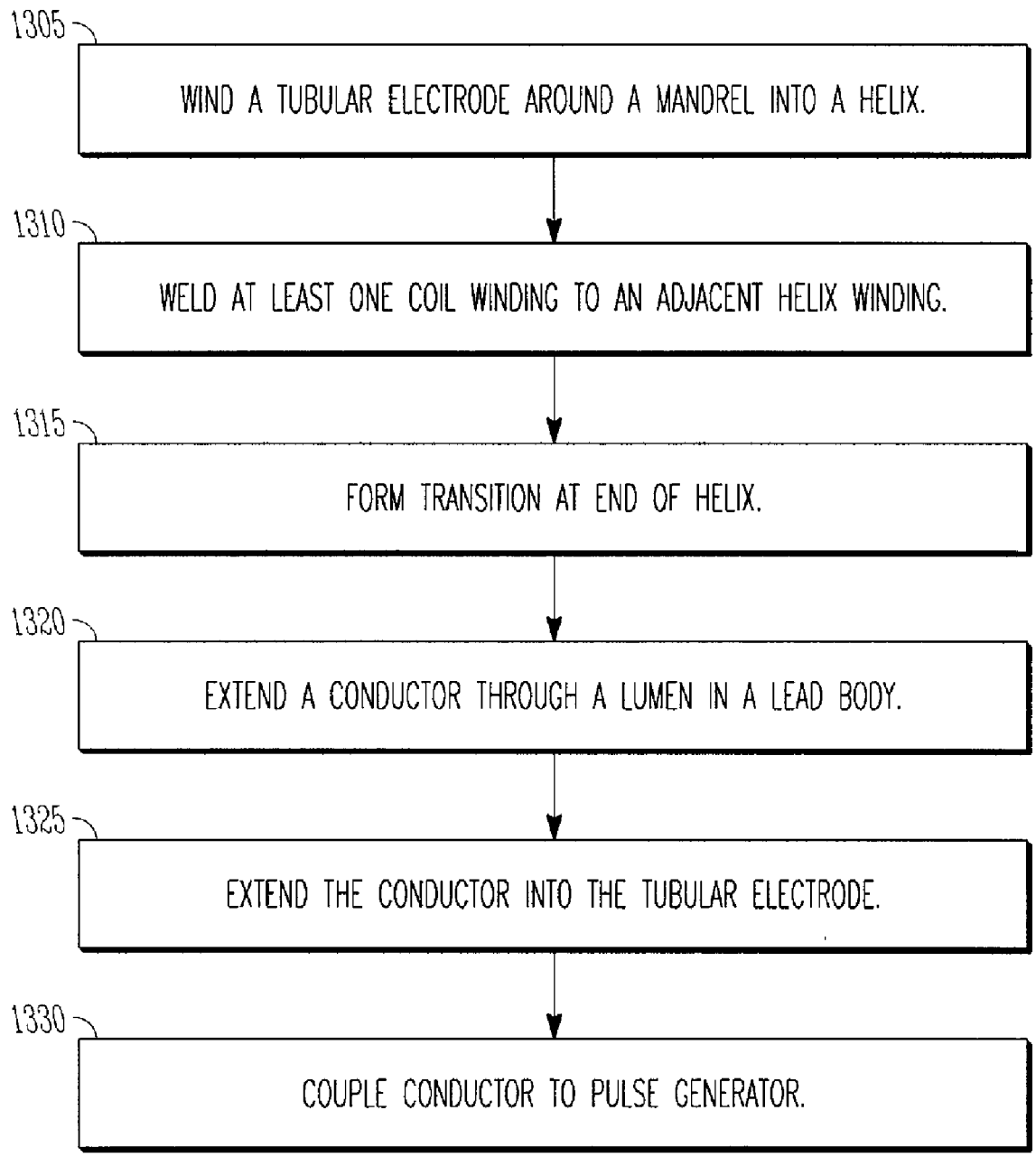
FIG. 13 is a flow chart that illustrates an example method that includes extending a conductor into a tubular electrode.

FIG. 13 illustrates an example method. At 1305, a tubular electrode is wound around a mandrel to form a helix. At 1310, at least one helical winding is optionally welded or otherwise connected to an adjacent helical winding. At 1315, a transition is optionally formed at one or both ends of the helix. In an example, a transition bends to be increasingly parallel with a helix axis, which reduces stress risers in a conductor if a conductor is extend into the tubular helix. At 1320, a conductor is extended through a lead body. At 1325, the conductor is extended into the tube. In an example, the conductor is extended into the tube after the conductor is extended through the lead body. In an example, a distal end of a conductor is pulled out of a lumen, inserted into the helical tubular electrode, and then the distal end of the conductor is placed back into the lumen. In another example, the conductor is extended into the tube before the conductor is extended through the lead body. In an example, the conductor is extended all the way through the tube, and optionally extended out of a distal end of the tube and back into the lead body. In an example, the conductor is formed into a helix that has a pitch and diameter that approximately matches the pitch and diameter of the helix of the tubular electrode. The electrode and/or conductor is turned as the helical conductor is inserted into the tubular electrode. In another example, a straight conductor is inserted into the helical tube, and the straight conductor is urged into a helix shape by the tube as it is advanced into the tube. At 1330, the conductor is optionally coupled to a pulse generator, such as a pulse generator in a defibrillator or other cardiac therapy device.

Figure 14:
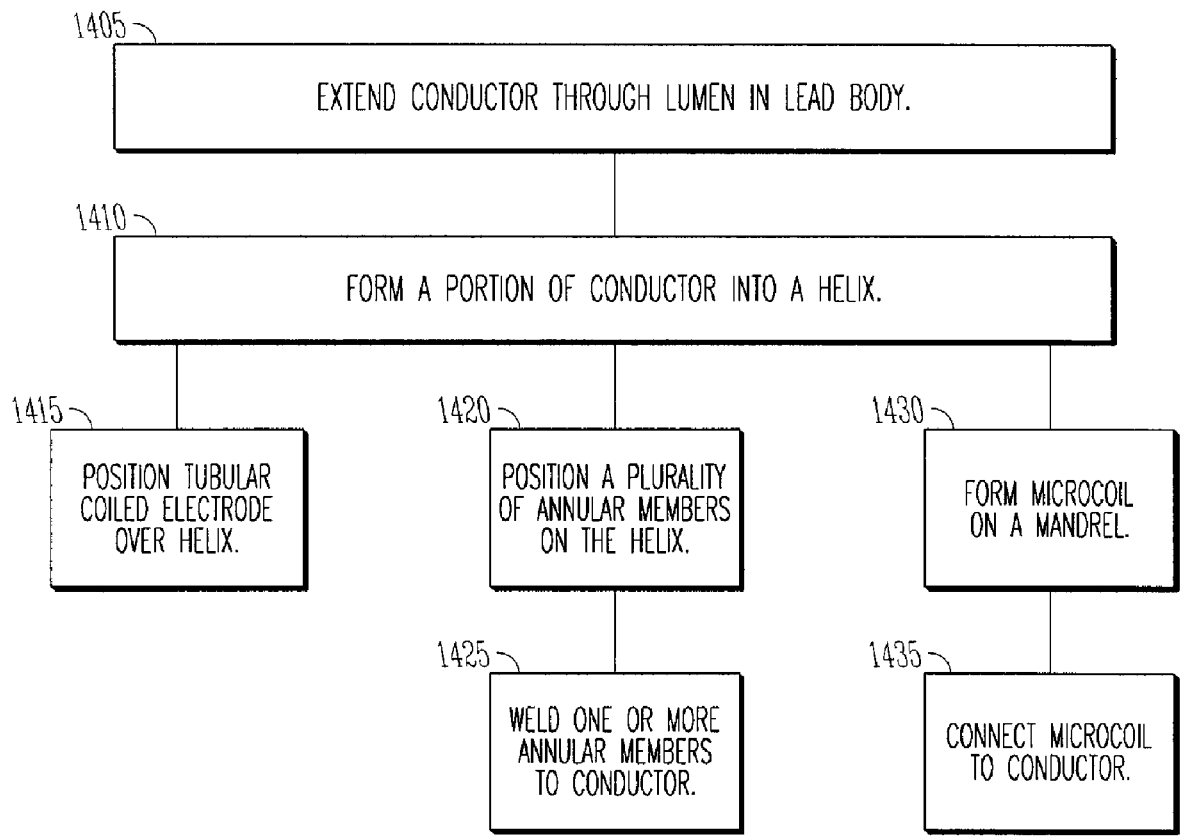
FIG. 14 is a flow chart that illustrates an example method that includes forming a portion of a conductor into a helix.

FIG. 14 illustrates additional example methods. At 1405, a conductor is extended through a lumen in a lead body. At 1410, a portion of the conductor is formed into a helix. At 1415, a tubular helical electrode is positioned over the helical portion of the conductor. Alternatively, at 1420, a plurality of annular members are positioned on the helical portion of the conductor. At 1425, one or more of the annular members is optionally welded to the conductor. In an example, an annular member at a distal end of a sequence of members is welded to the conductor. In an example, an annular member at a proximal end of the sequence of members is also welded to the conductor, so that members between the proximal and distal members are secured on the conductor. In another example, at 1430, a microcoil is formed on a mandrel, and the conductor is then extended through the microcoil. At 1435, one or more ends or other portions of the microcoil are optionally connected to the conductor. In an example, connecting the ends of the microcoil to the conductor and/or other filars prevents tissue abrasion associated with sharp filar ends. In an example, laser bonding is used to connect the microcoil to the conductor or other filars. In an example, connecting the microcoil to the conductor secures an electrical connection between the microcoil and conductor. Alternatively, an electrical connection between the microcoil and the conductor is created using a spring force in the microcoil and/or in the conductor. In an example, deformation of the conductor or microcoil creates spring forces that push the conductor and microcoil together. In an example, the use of spring forces to create an electrical connection simplifies manufacturing and validation, because welding or other processed are eliminated.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A lead assembly comprising:
an implantable lead body including a lumen;
a conductor extending through the lumen in the lead body; and
a helical electrode including a elongated, conductive tubular body having a continuous conductive surface extending between a first end and a second end and a lumen extending between the first and second ends defining an inner surface of the elongated, conductive tubular body, the elongated, conductive tubular body at least partially wound around an exterior surface of the implantable lead body, the helical electrode expandable from a first shape to a second shape, the conductor extending from the lead body into the first end of the elongated, conductive tubular body and electrically coupled to the elongated conductive tubular body such that the electrode is adapted to transmit one or more electrical signals between the exposed outer conductive surface of the tube and adjacent bodily tissue.

2. The lead assembly of claim 1, wherein the elongated, conductive tubular body is implantable in the compact shape and fixateable against a vessel wall in the expanded second shape upon implantation.

3. The lead assembly of claim 2, wherein the elongated, conductive tubular body includes a shape memory alloy and the elongated, conductive tubular body is expandable from the compact shape to the expanded second shape by application of heat to the shape memory alloy.

4. The lead assembly of claim 2, wherein the elongated, conductive tubular body is formed from a spring material.

5. The lead assembly of claim 2, wherein the lead body is coupled to the elongated, conductive tubular body, and the lead body is shapeable by expansion of the tube from the compact shape to the expanded second shape upon implantation.

6. The lead assembly of claim 1, wherein the elongated, conductive tubular body is elastically radially compressible, the lead assembly further comprising a sleeve extending over a portion of the elongated, conductive tubular body, the sleeve having an inner surface compressing a portion of the elongated, conductive tubular body and a slot the outer surface of the elongated, conductive tubular body to transmit electrical signals to or from adjacent bodily tissue.

7. The lead assembly of claim 6, wherein the lead body has a first portion having a first diameter and a second portion having a second diameter that is smaller than the first diameter, the elongated, conductive tubular body extending helically around an outer surface of the second portion of the lead body and the sleeve having an outer diameter approximately the same as the first diameter of the first portion of the lead body.

8. The lead assembly of claim 3, wherein the shape memory alloy includes Nitinol.

9. A lead assembly comprising:
an implantable lead body including at least one lumen and having an outer surface;
a conductor extending through the lumen in the lead body; and
a first helical electrode including a first elongated, conductive tube at least partially wound around the outer surface of the lead body, the first elongated conductive tube including a plurality of adjacent tubular segments each of which comprises a lumen defining an internal surface and an external conductive surface, a portion of the conductor extending into the lumen of at least one tubular segment and electrically coupled to the internal surface of the tubular segment,
the internal and external surfaces of the plurality of adjacent tubular segments extending around the outer surface of the lead body such that a portion of at least one external conductive surface contacts at least a portion of the outer surface of the lead body.

10. The lead assembly of claim 9, further comprising a second electrode including a second tube having an internal surface, a portion of the conductor extending into the second tube and electrically coupled to the internal surface of the second tube.

11. The lead assembly of claim 9, further comprising a second conductor extending through a lumen in the lead body, and a second electrode coupled to the second conductor, the second electrode electrically isolated from the first electrode.

12. The lead assembly of claim 9, wherein the tube includes a mesh.

13. The lead assembly of claim 9, wherein the conductor includes a cable comprising a plurality of filars.

14. The lead assembly of claim 9, wherein the lead assembly further comprises a cable including the conductor and at least one additional conductor.

15. The lead assembly of claim 9, further comprising a sleeve including a helix-shaped slot, the plurality of adjacent tubular segments disposed in the slot.

16. A lead assembly comprising:
an implantable lead body including a lumen;
a conductor extending at least partially through the lumen in the lead body; and
a first electrode including a first elongated, conductive tube helically wrapped around an outer surface portion of the lead body, the first elongated, conductive tube including continuous outer conductive surface extending between a first end, a second end and a lumen extending between the first end and the second ends, the lumen having an internal surface defining a helical path outside the outer surface portion of the lead body into which the conductor is inserted into the first end of the first elongated, conductive tube and extends through the first elongated, conductive tube to the second end and is electrically coupled to the first elongated, conductive tube such that the first electrode is adapted to transmit one or more electrical signals to adjacent bodily tissue.

17. The lead assembly of claim 16, wherein the first helical electrode is a defibrillation coil.

18. The lead assembly of claim 16, wherein the first elongated, conductive tube includes a first winding and a second winding adjacent to the first winding, the first winding connected to the second winding.

19. The lead assembly of claim 16, wherein a portion of the first elongated, conductive tube proximate an end into which the electrode transitions in a direction towards the conductor.

20. The lead assembly of claim 16, further comprising a second electrode including a second tube, the conductor extending through the second tube.

21. The lead assembly of claim 16, further comprising a second electrode including a second tube and a second conductor electrically coupled to the second tube.

22. The lead assembly of claim 16, wherein a first portion of the first elongated, conductive tube helically wrapped around the outer surface portion of the lead body has a first pitch and a second portion of the first elongated, conductive tube has a second pitch different from the first pitch.

23. A lead assembly comprising:
   a lead body;
   an electrode coupled to the lead body, the electrode including a helically wound elongated member forming a microcoil defining a passage on an inner portion and electrically communicating with adjacent bodily tissue on an outer portion, the passage extending around an outer surface portion of the lead body; and
   a conductor coupled to the lead body and extending through the passage defined by the microcoil, such that both the conductor and microcoil are helically wrapped around an outer surface portion of the lead body.

24. The lead assembly of claim 23, wherein an end of the microcoil is connected to the conductor.

25. The lead assembly of claim 23, further comprising a porous material extending over at least a portion of the microcoil.

26. The lead assembly of claim 23, wherein the conductor is a cable and wherein the microcoil extends helically around the conductor.

27. The lead assembly of claim 23, wherein the electrode further comprises a portion of the conductor.

* * * * *